(12) United States Patent
Dong et al.

(10) Patent No.: US 6,956,204 B2
(45) Date of Patent: Oct. 18, 2005

(54) DETERMINING FLUID PROPERTIES FROM FLUID ANALYZER

(75) Inventors: Chengli Dong, Pearland, TX (US); Peter S. Hageman, Houston, TX (US); Oliver C. Mullins, Ridgefield, CT (US); Go Fujisawa, Danbury, CT (US); Soraya S. Betancourt, Ridgefield, CT (US); Julian Pop, Houston, TX (US); Andrew L. Kurkjian, Sugar Land, TX (US); Toru Terabayashi, Kanagawa-ken (JP); Hani M. Elshahawi, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 94 days.

(21) Appl. No.: 10/249,274

(22) Filed: Mar. 27, 2003

(65) Prior Publication Data

US 2004/0193375 A1 Sep. 30, 2004

(51) Int. Cl.$^7$ ................................................ G01V 5/00
(52) U.S. Cl. ........................ 250/256; 702/13; 73/152.26
(58) Field of Search ............................... 702/13, 152.22, 702/152.18, 152.29; 250/256, 269.1, 255, 326; 73/152.26, 152.22, 152.18, 152.29; 356/436

(56) References Cited

U.S. PATENT DOCUMENTS

| 4,492,862 A | * | 1/1985 | Grynberg et al. ........... 250/255 |
| 4,788,852 A | | 12/1988 | Martin et al. |
| 4,860,581 A | | 8/1989 | Zimmerman et al. .... 73/152.26 |

(Continued)

FOREIGN PATENT DOCUMENTS

| WO | WO 98/36274 | 8/1998 |
| WO | WO 00/50876 | 8/2000 |
| WO | WO 02/079808 | 10/2002 |

OTHER PUBLICATIONS

Oliver C. Mullins et al., "Real–Time Determination of Filtrate Contamination during Openhole Wireline Sampling by Optical Spectroscopy," *SPE 63071*, SPE Annual Technical Conference and Exhibition, Dallas, TX (Oct. 1–4, 2000).

Finn Hallstein Fadnes et al., "Optimization of Wireline Sample Quality by Real–Time Analysis of Oil–Based Mud Contamination–Examples from North Sea Operations," *SPE 71736*, SPE Annual Technical conference and Exhibition, New Orleans, LA (Sep. 30–Oct. 3, 2001).

(Continued)

*Primary Examiner*—John Barlow
*Assistant Examiner*—Victor J. Taylor
(74) *Attorney, Agent, or Firm*—J. L. Jennie Salazar; Victor H. Segura; Brigitte L. Echols

(57) ABSTRACT

A method for determining properties of a formation fluid including obtaining data related to an optical density at a methane peak and an optical density at an oil peak for a fluid sample at a plurality of times, calculating an apparent gas-oil-ratio of the sample fluid from the optical density of the fluid sample at the methane peak to the optical density of the fluid sample at the oil peak at each of the plurality of times based on the data, selecting a power function of a sampling parameter for a buildup of the apparent gas-oil-ratio, calculating an exponential constant of the power function based on the data, and determining at least one selected from the group consisting of a contamination free gas-oil-ratio and a percent contamination.

30 Claims, 14 Drawing Sheets

U.S. PATENT DOCUMENTS

| | | | | |
|---|---|---|---|---|
| 4,936,139 | A | | 6/1990 | Zimmerman et al. ..... 73/152.26 |
| 4,961,343 | A | | 10/1990 | Boone ...................... 73/152.03 |
| 5,166,747 | A | * | 11/1992 | Schroeder et al. ........... 356/326 |
| 5,266,800 | A | * | 11/1993 | Mullins ....................... 250/256 |
| 5,331,156 | A | | 7/1994 | Hines et al. ................. 250/256 |
| 5,859,430 | A | * | 1/1999 | Mullins et al. .............. 250/255 |
| 5,939,717 | A | * | 8/1999 | Mullins ....................... 250/255 |
| 6,178,815 | B1 | | 1/2001 | Felling et al. ............ 73/152.26 |
| 6,218,662 | B1 | * | 4/2001 | Tchakarov et al. ........... 250/256 |
| 6,274,865 | B1 | * | 8/2001 | Schroer et al. ........... 250/269.1 |
| 6,350,986 | B1 | * | 2/2002 | Mullins et al. ........... 250/269.1 |
| 6,437,326 | B1 | * | 8/2002 | Yamate et al. ............ 250/269.1 |
| 6,474,152 | B1 | * | 11/2002 | Mullins et al. ........... 73/152.22 |
| 6,476,384 | B1 | * | 11/2002 | Mullins et al. ........... 250/269.1 |
| 6,627,873 | B2 | | 9/2003 | Tchakarov et al. ........... 250/256 |
| 6,707,556 | B2 | * | 3/2004 | Turner et al. ................. 356/436 |
| 6,768,105 | B2 | * | 7/2004 | Mullins et al. ........... 250/269.1 |
| 2001/0035312 | A1 | * | 11/2001 | Han et al. .................... 181/115 |
| 2002/0140425 | A1 | * | 10/2002 | Prammer et al. ........... 324/303 |
| 2004/0178336 | A1 | * | 9/2004 | DiFoggio ................. 250/269.1 |

OTHER PUBLICATIONS

C. Dong et al., "In–Situ Contamination Monitoring and GOR Measurement of Formation Fluid Samples," *SPE 77899*, SPE Asia Pacific Oil and Gas Exhibition, Melbourne, Australia (Oct. 8–10, 2002).

A Crombie et al., "Innovations in Wireline Fluid Sampling," *Oilfield Review*, pp. 26–41 (Autumn 1998).

AR Smits et al., "In–Situ Optical Fluid Analysis as an Aid to Wireline Formation Sampling," *SPE Formation Evaluation*, pp. 91–98 (Jun. 1995).

MN Hashem et al., "Determination of Producible Hydrocarbon Type and Oil Quality in Wells drilled with Synthetic Oil–Based Muds," *SPE Reservoir Evaluation & Eng. 2 (2)*, pp. 125–133 (Apr. 1999).

Oliver C. Mullins et al., "Real–Time Determination of OBM Filtrate Contamination during Openhole Wireline Sampling," *SPE 70479*, pp. 24–26 (Feb. 2001).

* cited by examiner

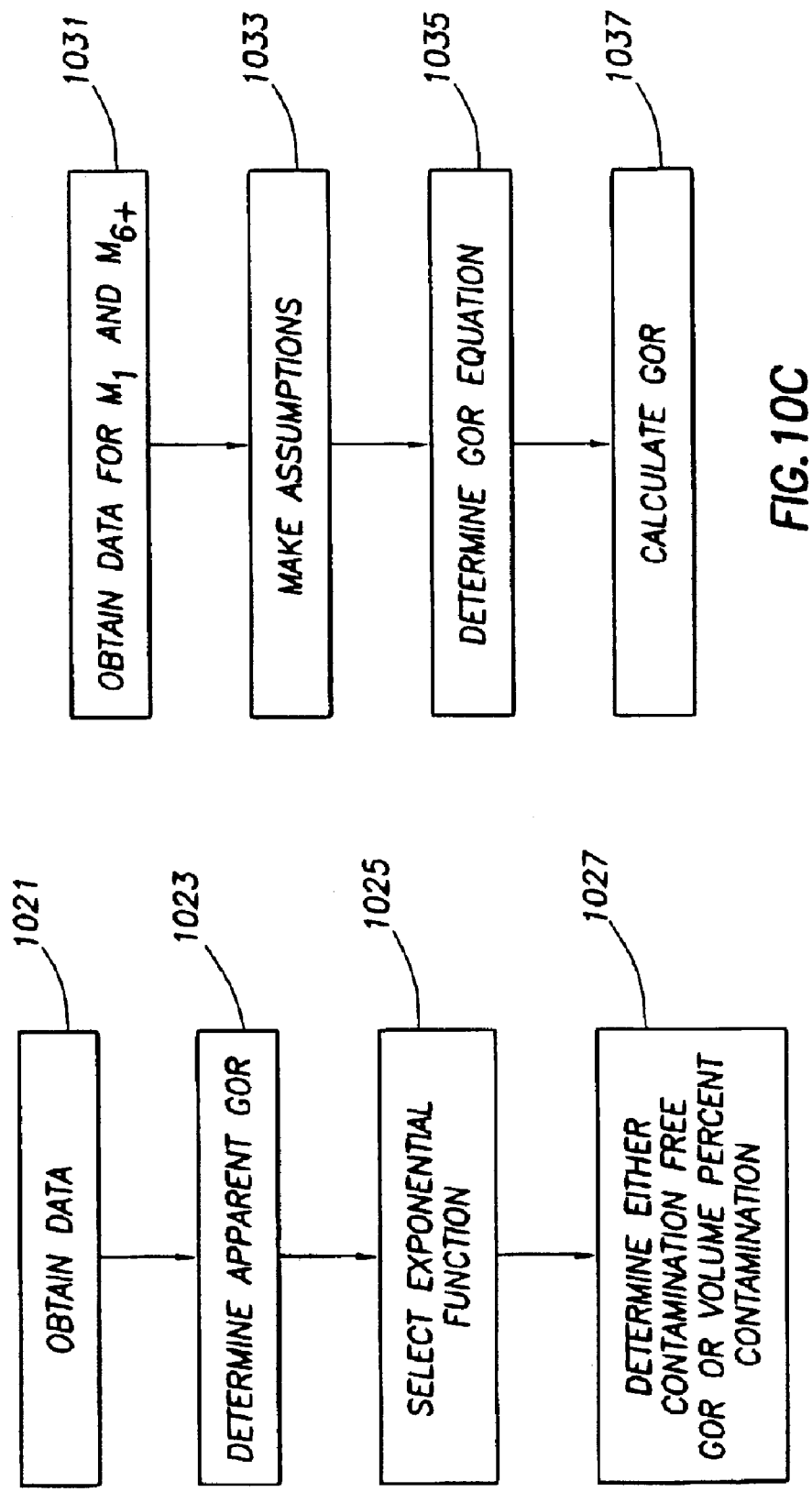

DETERMINING FLUID PROPERTIES FROM FLUID ANALYZER

BACKGROUND OF INVENTION

Wells are generally drilled into the ground to recover natural deposits of hydrocarbons and other desirable materials trapped in geological formations in the Earth's crust. A well is drilled into the ground and directed to the targeted geological location from a drilling rig at the Earth's surface.

Once a formation of interest is reached in a drilled well, drillers often investigate the formation fluids by taking fluid samples from the formations for analysis. The analysis of a fluid sample provides information about the fluid's contents, density, viscosity, bubble point, and other important characteristics. This vital information is used for field planning decisions and for the optimization of upstream and downstream production facilities.

One fluid characteristic of particular importance is the gas-oil-ratio ("GOR"). The GOR is the ratio of the volume of the gaseous phase in the native formation fluids over the volume of liquid hydrocarbons at the standard conditions (standard conditions are 60° F. and 1 atm). Typical units for GOR are standard cubic feet of gas per barrel of oil at the standard conditions (scf/bbl), that is cubic feet of gas per barrel of oil at the standard conditions. The GOR is important in designing the upstream and downstream production facilities. For example, if the GOR is high, the surface facilities must be designed to handle a large amount of gas from the well.

Typically, a fluid sample is obtained by lowering a fluid sampling tool into the well and withdrawing a fluid sample from an underground formation. One example of a sampling tool is the Modular Formation Dynamics Tester (MDT), which is a registered trademark of Schlumberger Technology Corporation, the assignee of this invention. Formation testing tools are disclosed in U.S. Pat. Nos. 4,860,581 and 4,936,139 to Zimmerman et. al, which are assigned to the assignee of the present invention.

FIG. 1 shows a formation testing tool 101 designed to withdraw a fluid sample from a formation 114. The tool 101 is suspended in a borehole 110 on a conveyance 115 such as wireline, or multiconductor cable, that is spooled from the surface. At the surface, the wireline 115 is typically connected to an electrical control system 118 that monitors and controls the tool 101.

Once at a desired depth, the tool 101 is used to obtain a formation fluid sample. The tool 101 has a probe 120, or fluid admitting means, that is selectively extendable from the tool 101, as well as an anchoring member 121 on the opposite side of the tool 101 that is also selectively extendable. The probe 120 extends from the tool 101 and seals against the borehole wall 112 so that the probe 120 is in fluid communication with the formation 114. A typical tool 101 also includes a pump (not shown). The pump is used to pump formation fluids from the formation into the tool 101. The pump may also be used to pump formation fluids from the tool 101 into the borehole 110.

One of the problems associated with fluid sampling is that the formation fluid is typically contaminated with mud filtrate. Mud filtrate is a fluid component of the drilling fluid that seeps into the formation during the drilling process. The mud filtrate invades the formation and contaminates the native formation fluid. When a fluid sample is withdrawn from the formation, the sample will initially include mud filtrate.

To solve this problem, a fluid sample typically is withdrawn from the formation and pumped into the borehole or into a large waste chamber in the tool until the fluid being withdrawn has "cleaned up." A "cleaned up" sample is one where the concentration of mud filtrate in the sample fluid is acceptably low so that the fluid represents the native formation fluids. At that point, a sample may be collected for later analysis.

Referring to FIG. 1 again, formation fluid is withdrawn from the formation 114 by the probe 120, and the fluid passes through a fluid analyzer 125 before it is pumped out of the tool 101 and into the borehole by a pumping means (not shown). The fluid analyzer 125 analyzes the sample fluid to determine the level of mud filtrate contamination. Once the formation fluid being withdrawn through the probe is clean, a sample may be taken by pumping the fluid sample into one of the sample chambers 122, 123.

One type of fluid analyzer used in a formation testing tool is an optical sensor, which measures the optical density ("OD") of the sample fluid at several different wavelengths. The oil used in a oil-based mud ("OBM") typically is light in color, thus, as the sample fluid cleans up, the OD at the color channels increases asymptotically to the OD of the darker native formation fluid.

Two types of absorption mechanism contribute to the measured OD of a fluid sample: electron excitation and molecular vibration mode excitation. Absorption by electron excitation occurs when the energy of incident light is transferred to excite delocalized pi electrons to anti-bonding states. This energy level typically corresponds to visible to near-infrared range and gives a shade of color as a result. We simply refer this mode of absorption as color hereafter in this document. Oils may exhibit different colors because they have varying amounts of aromatics, resins, and asphaltenes, each of which absorb light in the visible and near-infrared ("NIR") spectra. Heavy oils have higher concentrations of aromatics, resins, and asphaltenes, which give them dark colors. Light oils and condensate, on the other hand, have lighter, yellowish colors because they have lower concentrations of aromatics, resins, and asphaltenes.

Molecular vibration absorption is the absorption of a particular frequency of light due to resonance of the chemical bonds in a molecule. While color absorption covers the visible and NIR spectrums, molecular vibration absorption occurs only at specific wavelengths for specific materials. For any given molecule, the wavelength at which vibration absorption occurs is related to the type of chemical bonds and the molecular structure. For example, oils have molecular vibration absorption peaks near wavelengths of 1,200 nm, 1,400 nm, and 1,700 nm. Molecular vibration absorption is a function of the concentration of the particular substance, and it is not necessarily affected by the phase of the substance. For example, the magnitude of a methane absorption resonance peak (near 1,670 nm) will be the same, regardless of whether the methane is in the gas phase or dissolved in the oil.

One type of optical sensor is the Optical Fluid Analyzer ("OFA"), which is a trademark of Schlumberger. The OFA measures the OD of the sample fluid at ten different wavelengths in the near-infrared ("NIR") and visible range. When fluid is first withdrawn from a formation, the sample fluid is comprised of mostly light colored OBM filtrate. As the sample fluid cleans up, the sample fluid will contain more of the darker native formation fluid. The OD of the fluid sample in color channels will change as the fluid cleans up. For example, because the formation fluid is darker in color than the OBM filtrate, the OD of the fluid sample at the color channels will increase as the fluid sample is withdrawn. The OD at the color channels will asymptotically approach the OD of the formation fluid.

By taking OD data at multiple times, the OD of the native formation fluid, called the "contamination free" OD, can be mathematically determined by computing the asymptotic value of the measured OD. "Contamination free" is used herein to mean a property of the native formation fluid, substantially free of contamination from the mud filtrate. Thus, "contamination free GOR" means the GOR of the formation fluid, with no or insignificant effect from the mud filtrate. While it may be difficult in practice to obtain a fluid sample that is free of mud filtrate contamination, the goal is to determine the properties of the formation fluid. The term "apparent" is used to refer to the value of a measurement taken during a sampling process. Thus, the "apparent GOR" is the measured value of the GOR of a fluid sample that is withdrawn from the formation. The apparent GOR may be influenced by mud filtrate or other contaminants.

Once the contamination free OD is predicted, the amount of OBM filtrate contamination in the sample fluid may be determined based on the measured OD and the contamination free OD. Methods for determining the contamination of OBM in a fluid sample are disclosed, for example, in U.S. Pat. No. 5,266,800 to Mullins, which is assigned to the assignee of the present invention.

Another type of optical sensor is called the Live Fluid Analyzer ("LFA"), which is a trademark of Schlumberger. The LFA is different from the OFA because the LFA includes a methane channel at the wavelength of a "methane peak" and an oil channel at the wavelength of an "oil peak." A "methane peak" is a molecular vibration absorption peak of methane, whose wavelength corresponds to the resonance of the CH bond in a methane molecule, One methane molecular vibration absorption peak is at a wavelength of about 1,670 nm. The molecular vibration absorption occurs independently of the color of the fluid and independently of whether the methane is in the gas phase or dissolved in the formation fluid. Similarly, an "oil peak" is a molecular vibration absorption peak of oil, whose wavelength corresponds to the resonance of the combination of —$CH_2$ and —$CH_3$ groups in an oil molecule. One oil peak is at a wavelength of about 1,720 nm.

Typically, OBM contains no methane, so the OD at the methane peak will increase as the fluid sample is withdrawn from the formation. The OD of the methane peak will asymptotically approach the OD at the methane peak of the formation fluid. The OD of the fluid sample at the oil channel may increase or decrease, depending on the composition of the formation fluid. Either way, it will asymptotically approach the OD at the oil channel of the formation fluid.

Another type of optical sensor is called the Condensate and Gas Analyzer ("CGA"), which is a trademark of Schlumberger. A CGA uses optical channels at specific frequencies to get a better estimate of the spectrum of gases present in a fluid sample. For example, a typical CGA has a channel that corresponds to the resonance peak for molecular vibration absorption in carbon dioxide. A typical CGA is able to determine mass concentrations of methane, non-methane gaseous hydrocarbons, carbon dioxide, and liquid hydrocarbons.

While these analyzers provide convenient methods for monitoring various components in formation fluids and, hence, the extent of the mud filtrate contamination in the formation fluids, it is desirable to have methods that are more sensitive and less influenced by pumping rates for such monitoring.

SUMMARY OF INVENTION

In one or more embodiments, the invention relates to a method for determining properties of a formation fluid comprising obtaining data related to an optical density at a methane peak and an optical density at an oil peak for a fluid sample at a plurality of times, and calculating an apparent gas-oil-ratio of the sample fluid from the optical density of the fluid sample at the methane peak and the optical density of the fluid sample at the oil peak at each of the plurality of times. The method then includes selecting a power function of a sampling parameter for a buildup of the apparent gas-oil-ratio, calculating an exponential constant of the power function based on the data, and determining at least one selected from the group consisting of a contamination free gas-oil-ratio and a percent contamination. In some embodiments, the sampling parameter may be selected from the elapsed time, the pumping time, and the pumpout volume.

In one or more embodiments the invention relates to a method for determining properties of a formation fluid comprising obtaining data related to an optical density at a methane peak and at an oil peak for a fluid sample at a plurality of times, calculating an apparent gas-oil-ratio of the sample fluid at the plurality of times based on the data, and selecting an exponential function of a sampling parameter for a buildup of the apparent gas-oil-ratio. The method then includes linearly extrapolating the gas-oil-ratio to a point where a derivative of the exponential function with respect to the sampling parameter is zero. In some embodiments, the sampling parameter may be selected from the elapsed time, the pumping time, and the pumpout volume.

In one or more embodiments, the invention relates to a method for determining a gas-oil-ratio of a fluid sample comprising obtaining data related to a methane mass component, a non-methane gaseous hydrocarbon mass component, a liquid phase hydrocarbon mass component, and a carbon dioxide mass component at a plurality of times. The method then includes determining the gas-oil-ratio from the ratio of the methane mass component, the non-methane gaseous hydrocarbon mass component, and the carbon dioxide mass component to the liquid phase hydrocarbon mass component. In some embodiments, the gas-oil-ratio is determined using a function of the methane mass concentration, the non-methane gaseous hydrocarbon mass component, the liquid phase hydrocarbon mass component, and the carbon dioxide mass component. In at least one embodiment, the function is based on assumptions about formation fluid components.

In one or more embodiments, the invention relates to a method for determining properties of a formation fluid comprising obtaining data related to a mass concentration of methane and a mass concentration of liquid phase hydrocarbons for a fluid sample at a plurality of times, and calculating an apparent methane mass concentration and an apparent liquid phase hydrocarbon mass concentration of the fluid sample at each the plurality of times. The method then includes selecting a methane power function of a sampling parameter for a buildup of the apparent methane mass concentration, selecting a liquid phase power function of a sampling parameter for a buildup or builddown of the apparent liquid phase hydrocarbon mass concentration, determining an exponential constant of the methane power function based on the data, determining an exponential constant of the liquid phase power function based on the data, and determining a volume percent contamination. In some embodiments, the sampling parameter may be selected from the elapsed time, the pumping time, and the pumpout volume.

In one or more embodiments, the invention relates to a method for determining properties of a formation fluid comprising obtaining data related to a mass concentration of methane and a mass concentration of liquid phase hydrocarbons for a fluid sample at a plurality of times, and calculating an apparent methane mass concentration and an apparent liquid phase hydrocarbon mass concentration of the fluid sample at each of the plurality of times. The method then includes selecting a methane exponential function of a sampling parameter for a buildup of the apparent methane mass concentration, selecting a liquid phase exponential function of the sampling parameter for a buildup or builddown of the apparent liquid phase hydrocarbon mass concentration, and determining a volume percent contamination from the data. In some embodiments, the sampling parameter may be selected from the elapsed time, the pumping time, and the pumpout volume.

BRIEF DESCRIPTION OF DRAWINGS

FIG. 10B shows another embodiment of a method according to the invention.

FIG. 10C shows another embodiment of a method according to the invention.

DETAILED DESCRIPTION

In certain embodiments, the present invention relates to methods for determining contamination free properties of a fluid sample and monitoring the contamination level in a fluid sample. The apparent gas-oil-ratio ("GOR") of a fluid sample may be used to determine the contamination free GOR of the formation fluid and to monitor the contamination of a fluid sample. Further, in some embodiments, the invention relates to methods for determining the apparent GOR of a fluid sample using a Condensate and Gas Analyzer ("CGA"). The CGA may also be used to monitor the contamination of a fluid sample.

While the present invention is particularly useful, and is described herein, for fluid sampling from wells drilled with an oil-based mud ("OBM"), those having ordinary skill in the art will realize that embodiments of the invention may be applied to fluid sampling in wells drilled with other types of mud, such as a water-based mud ("WBM"). The present invention is also applicable to both borehole investigative logging and production logging. For purposes of brevity, the description is directed to borehole investigative logging of wells drilled using an OBM. It will be understood that the invention may be used in other situations.

Contamination Free GOR

Some embodiments of the present invention may be used to determine the contamination free GOR of a fluid sample. In one or more embodiments, the present invention relates to monitoring the contamination of a fluid sample using an apparent GOR and the contamination free GOR.

In general, the oil in an OBM contains virtually no methane or other dissolved gases. Thus, the GOR of an OBM is essentially zero. Formation oils, on the other hand, can have a GOR that ranges from less than 20 scf/bbl, for heavy black oils, to more than 30,000 scf/bbl, for condensate. When a sampling process is begun, the fluid sample first withdrawn from the formation is mostly comprised of mud filtrate and the measured GOR is essentially zero. As the sampling process continues, the apparent GOR asymptotically builds up to the GOR of the formation fluid.

Figure 1:
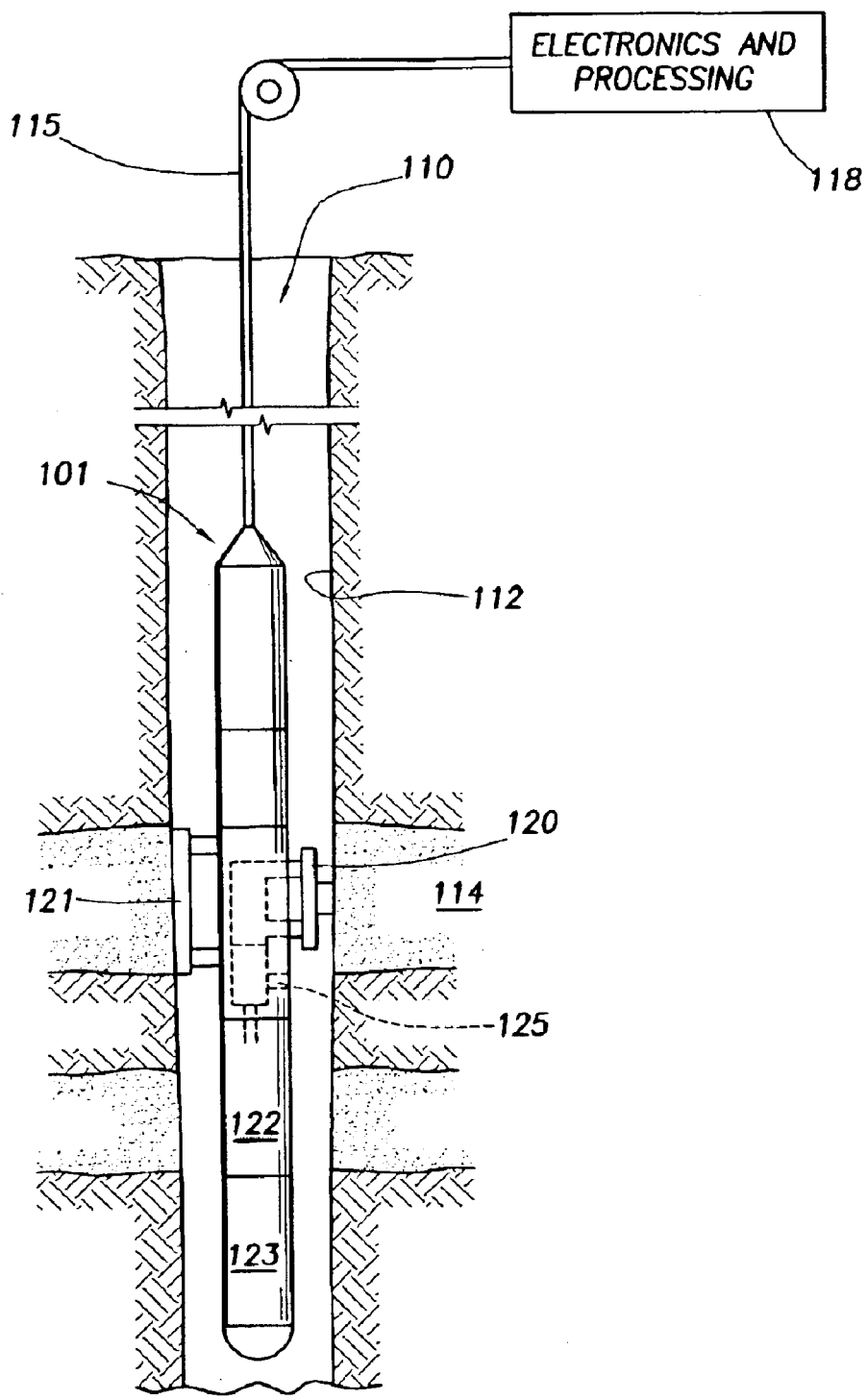
FIG. 1 shows a cross-section of a prior art formation testing tool.
Figure 2A:
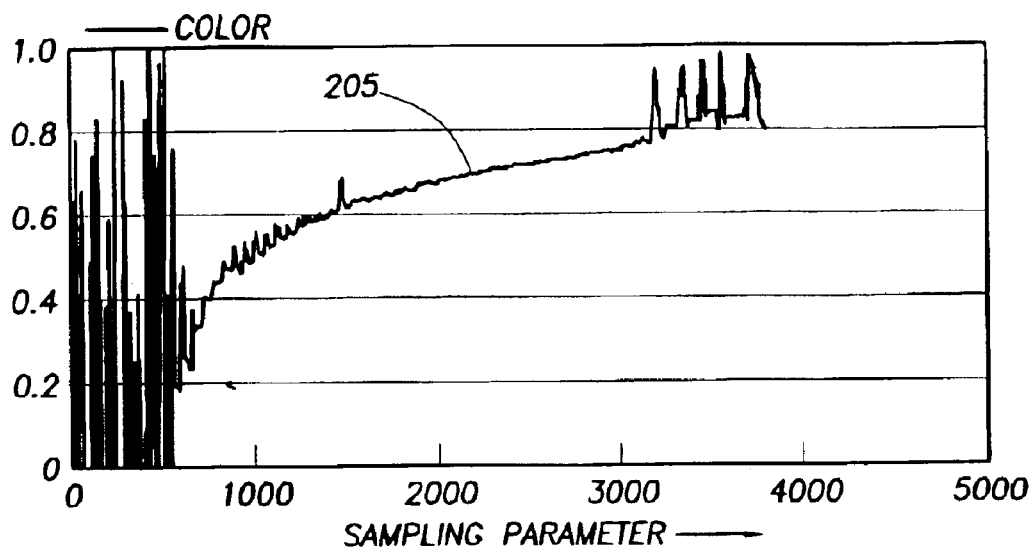
FIG. 2A shows a plot of data from a color channel for a fluid sample.
Figure 2B:
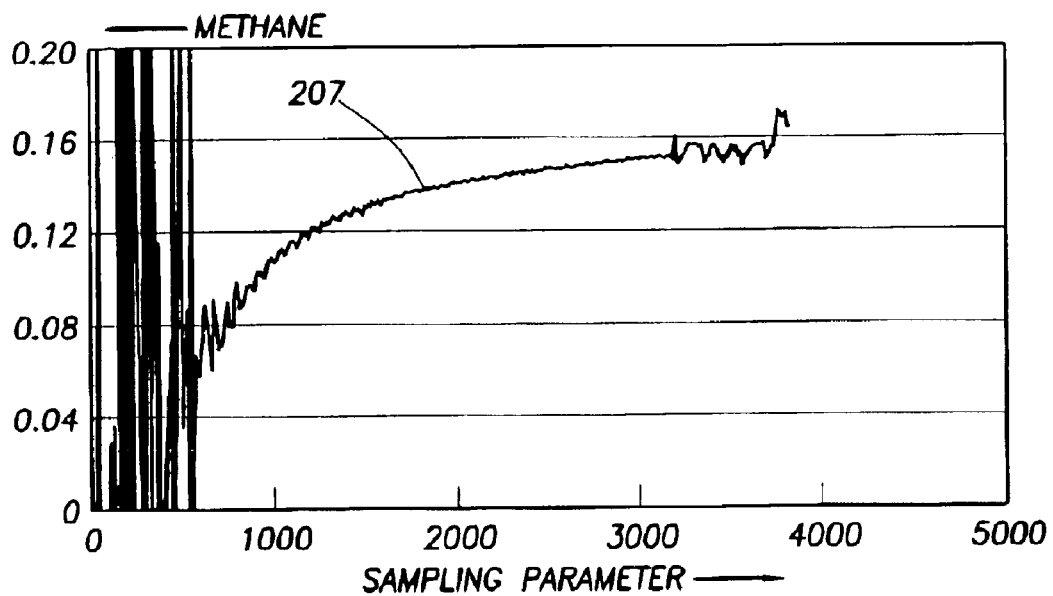
FIG. 2B shows a plot of data from a methane channel for a fluid sample.

FIGS. 2A–B show examples of graphs of the OD in several channels of an LFA tool versus pumping time during a sampling process. It will be understood that pumping time is only one variable that may be used when monitoring the OD of a fluid sample is various channels.

FIG. 2A shows a plot 205 of the color channel. The color channel plot 205 shows that the OD due to the color of the fluid builds up as the fluid sample is withdrawn from the formation. Similarly, FIG. 2B shows a plot 207 of the methane channel. The plot 207 shows that the OD due to methane molecular vibration absorption also builds up as the fluid sample is withdrawn from the formation. Both the color channel and the methane channel plots 205, 207 build up asymptotically to their contamination free values. Several prior art methods have been developed to determine the level of contamination from the color and methane channels.

The GOR can be determined using a fluid analyzer having a methane channel and an oil channel. The GOR is calculated from the ratio of the amplitude of the methane peak to the amplitude of the oil peak. One method for determining the GOR uses the equation GOR=8930[$m_m$/($m_o$−0.1 93 $m_m$)]; where $m_m$ is the mass fraction of methane, $m_o$ is the mass fraction of oil, and the units are scf/bbl. Methods for determining the GOR are disclosed in SPE 77899 "In-Situ Contamination Monitoring and GOR Measurement of Formation Fluid Samples," by Dong et al., presented in the SPE Technical Symposium held at Melbourne, Australia, on Oct. 10, 2002.

Figure 2C:
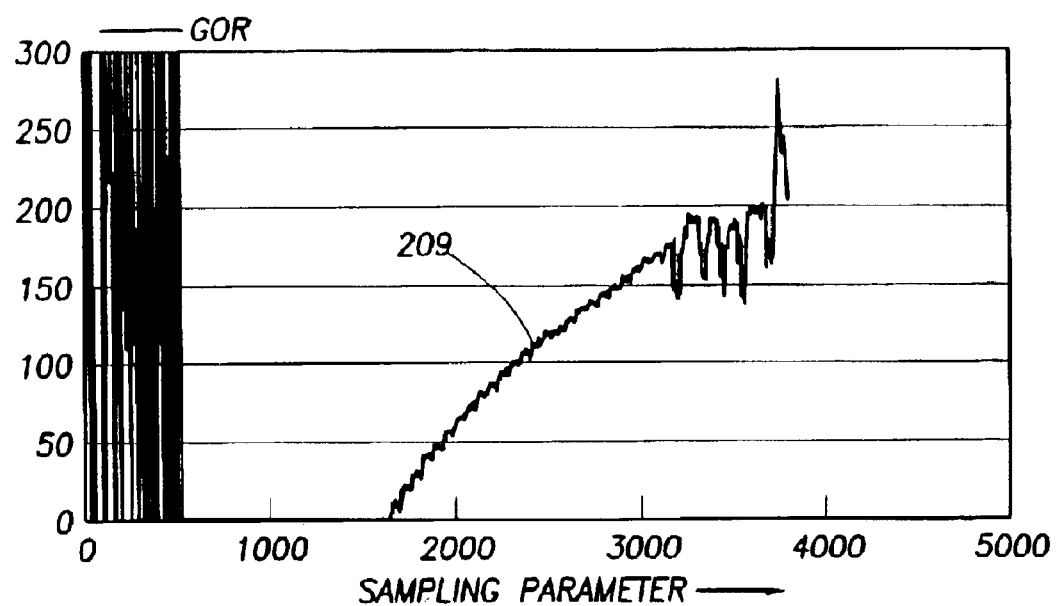
FIG. 2C shows a GOR plot for a fluid sample.

The apparent, or measured, GOR is shown in the GOR plot 209 in FIG. 2C. The apparent GOR is computed from the methane channel (plot 207 in FIG. 2B) and the oil channel (not shown). Consequently, the apparent GOR builds up much faster than the color channel or the methane channel, as is shown in the plot 209 in FIG. 2C.

Figure 2D:
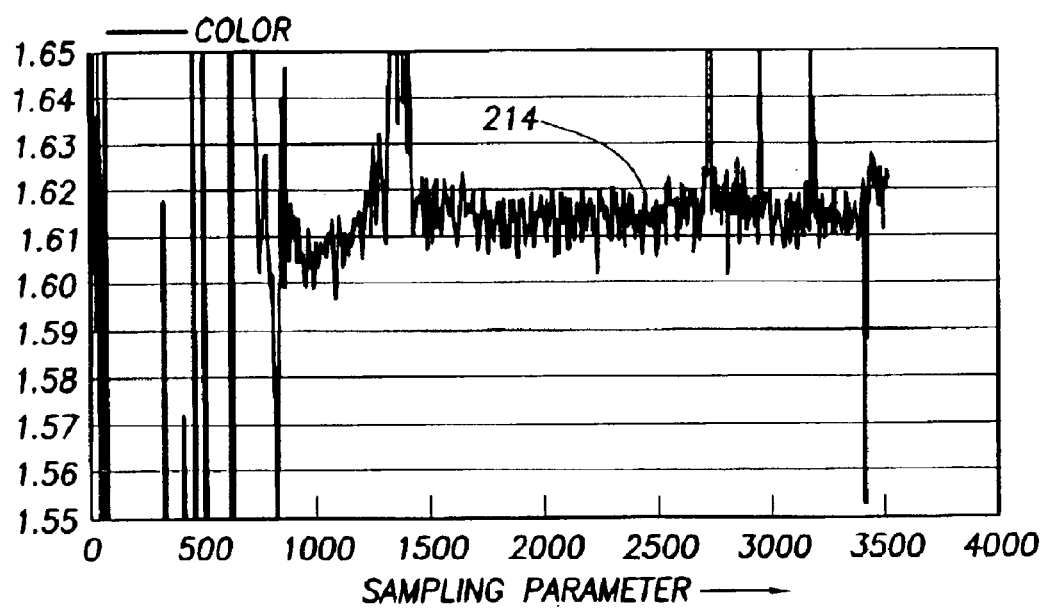
FIG. 2D shows a plot of data from a color channel for a fluid sample.
Figure 2E:
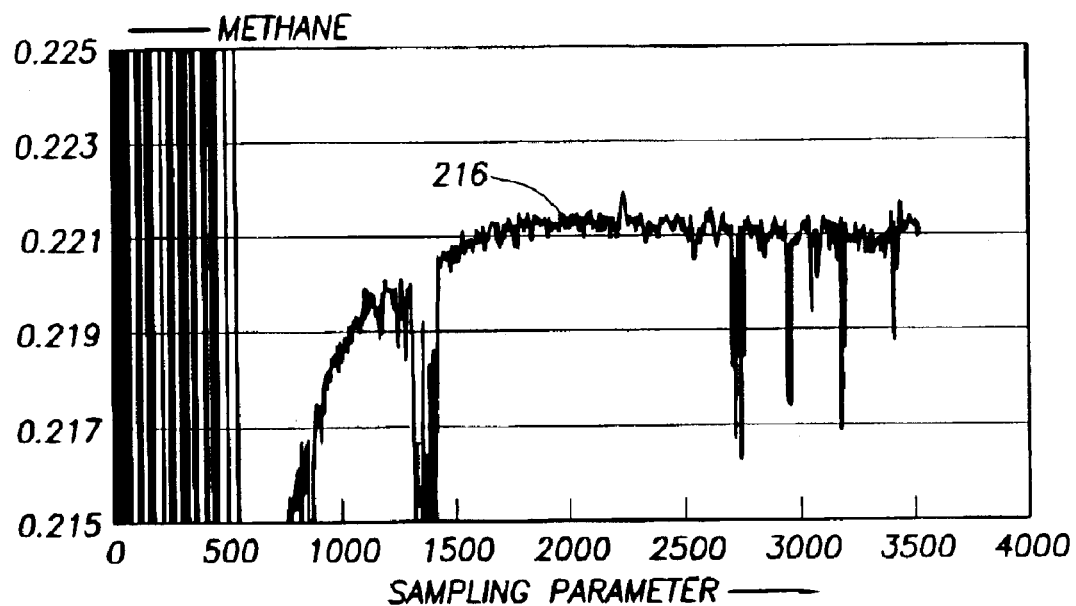
FIG. 2E shows a plot of data from a methane channel for a fluid sample.
Figure 2F:
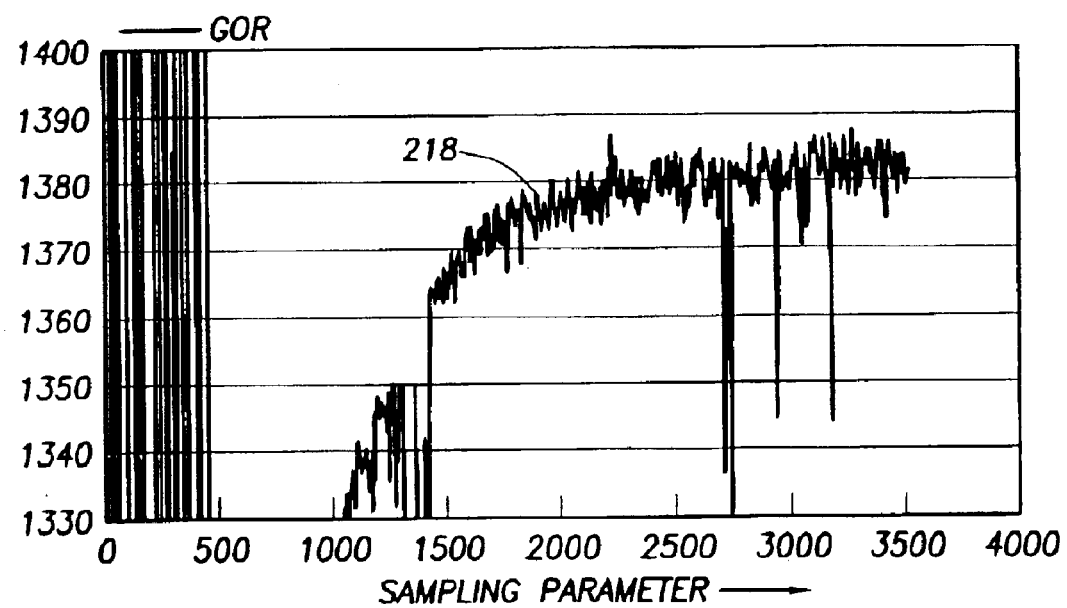
FIG. 2F shows a GOR plot for a fluid sample.

The increased rate of buildup of the apparent GOR enables the GOR measurement to be more sensitive to small changes in contamination. FIGS. 2D–2F show LFA data (versus, e.g., pumping time) taken where there is very little contamination in the fluid sample. The color channel plot 214 in FIG. 2D shows almost no buildup, and the methane channel plot 216 in FIG. 2E may even show a slight build down due to the low contamination levels. The apparent GOR (shown in GOR plot 218 in FIG. 2F), however, is more sensitive than either the color channel or the methane channel, and the apparent GOR graph 218 shows a buildup as the fluid sample is taken.

Figure 2G:
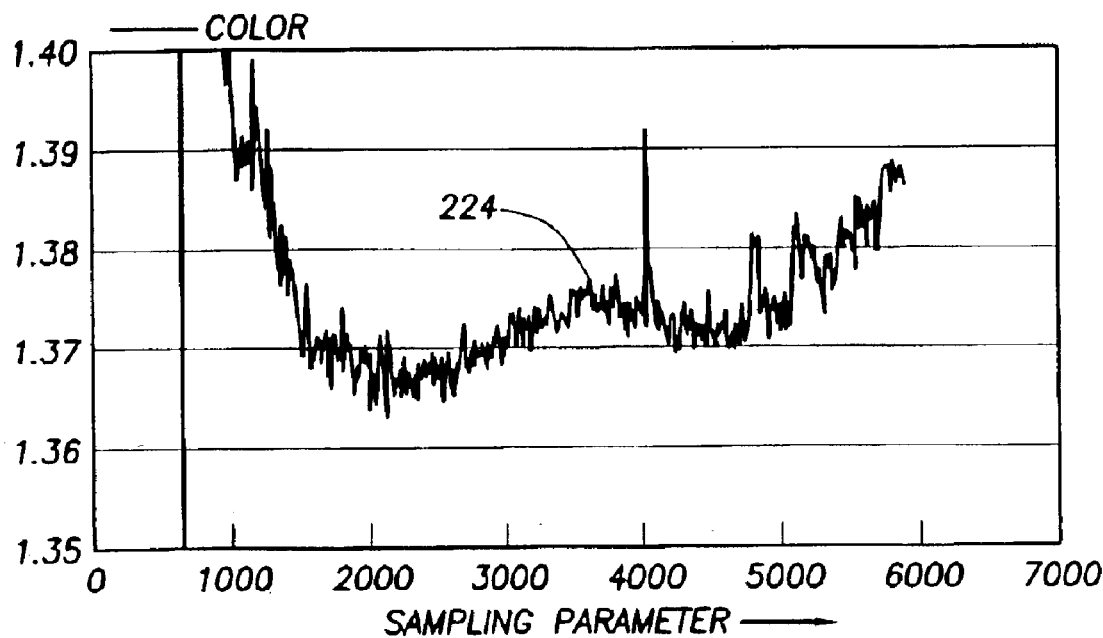
FIG. 2G shows a plot of data from a color channel for a fluid sample.
Figure 2H:
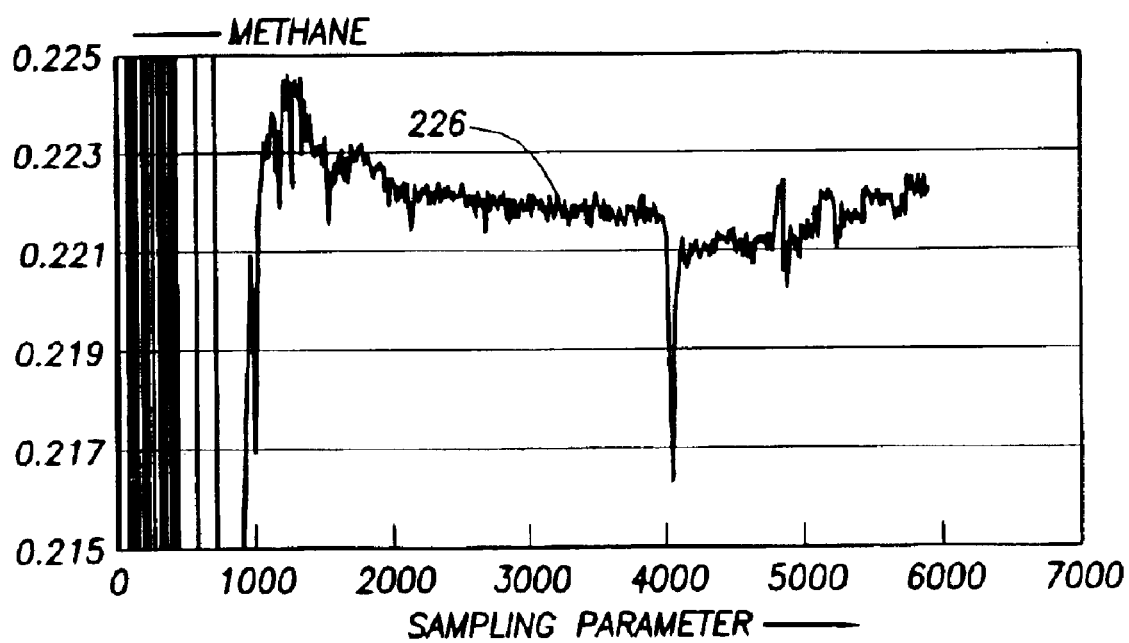
FIG. 2H shows a plot of data from a methane channel for a fluid sample.
Figure 2I:
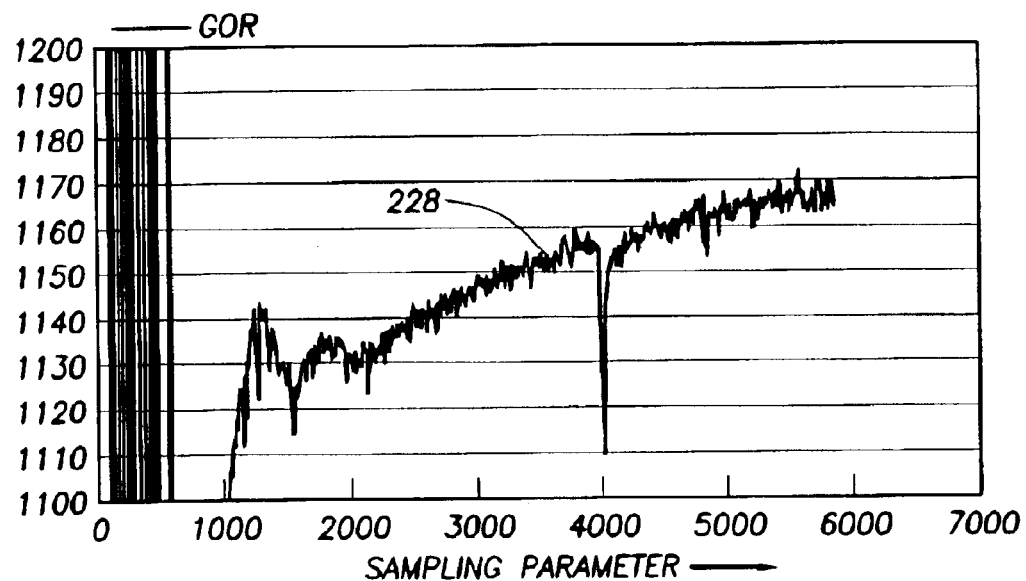
FIG. 2I shows a GOR plot for a fluid sample.

The pumping rate of the fluid sample may be changed during the sample taking process. For example, if the pressure is approaching the bubble point of the fluid sample, the pumping rate may be slowed to maintain the fluid sample pressure above its bubble point. FIGS. 2G–2I show graphs of LFA data (versus, e.g., pumping time) taken while the fluid pumping rate is changed. Both the color channel plot 224 in FIG. 2G and the methane channel plot 226 in FIG. 2H show a leveling or a build down when the pumping rate is slowed at about 4000. The apparent GOR plot 228 in FIG. 2I, however, shows a continuous buildup throughout the pumping process.

The buildup of GOR can be modeled as a function of a parameter of the sampling process. One such sampling parameter is pumping time. Pumping time is the total time that the pump is turned on and pumping fluid out of the formation. Thus, if the pump is stopped for any reason, the pump down time will not be included in pumping time. An equation for such a function may have the form GOR=f(t), where t represents the sampling parameter. In one or more embodiments, the GOR time function is modeled as a power function, as shown in Equation 1:

$$GOR = X - Yt^{-a} \qquad \text{Eqn. 1}$$

Where X is the contamination free GOR, Y is a constant related to the buildup of GOR, t is the pumping time, and a is an exponential constant.

It is noted that in the illustrative examples provided in this disclosure, t is used to denote pumping time, but other sampling parameters could be used in its place. For example, t may be used to designate elapsed time in those situations where the pump is run continuously at substantially the same rate. In another example, t could be used to designate pumpout volume. Those having ordinary skill in the art will realize that other sampling parameters may be used as t without departing from the scope of the present invention. For example, the sampling parameter may be elapsed time, pumping time, pumpout volume, or any other sampling parameter that represents the sampling process.

Taking the derivative of Equation 1 with respect to t yields:

$$\frac{d(GOR)}{dt} = aYt^{-a-1} \qquad \text{Eqn. 2}$$

Multiplying both sides of Equation 2 by t and rearranging the equation using the identity t/dt=1/d ln(t) gives:

$$\frac{d(GOR)}{d\ln(t)} = aYt^{-a} \qquad \text{Eqn. 3}$$

Finally, taking the natural logarithm of both sides gives:

$$\ln\left(\frac{d(GOR)}{d\ln(t)}\right) = \ln(a) + \ln(Y) - a\ln(t) \qquad \text{Eqn. 4}$$

Figure 3:
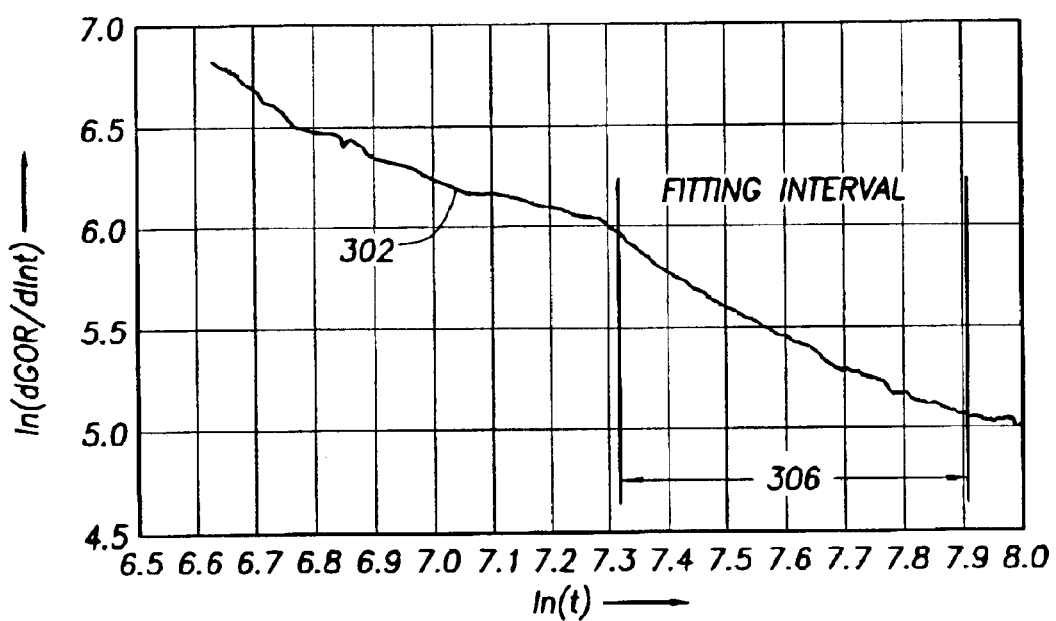
FIG. 3 shows a graph of the natural log of the GOR with respect to the natural log of a sampling parameter versus the natural log of the sampling parameter over a fitting interval.

Equation 4 shows that ln(d(GOR)/d ln(t)) has a linear relationship with ln(t). The exponential constant a may be determined using this relationship. FIG. 3 shows a graph of the left side of Equation 4, ln(d(GOR) d ln(t)), versus ln(t), using apparent GOR data collected as a fluid sample is taken. The exponential constant a can be determined as the slope of the line 302 in FIG. 3, over a selected fitting interval 306. In Equation 4, other than natural logarithm, any type of logarithm like $\log_n$ (n can be any positive number) can be used to determine the exponential constant a.

The fitting interval 306 may be automatically selected so that the data points in the fitting interval fit into a straight line. For example, the fitting interval 306 may be an automatically detected fitting interval in which the data points fall substantially on a line, and the Y-axis intercept can be extrapolated as in FIG. 4. Alternatively, the fitting interval 306 may be selected manually, for example, by selecting a substantially linear region in the graph. One of ordinary skill in the art will appreciate that various algorithms may be used to select a fitting interval.

Figure 4:
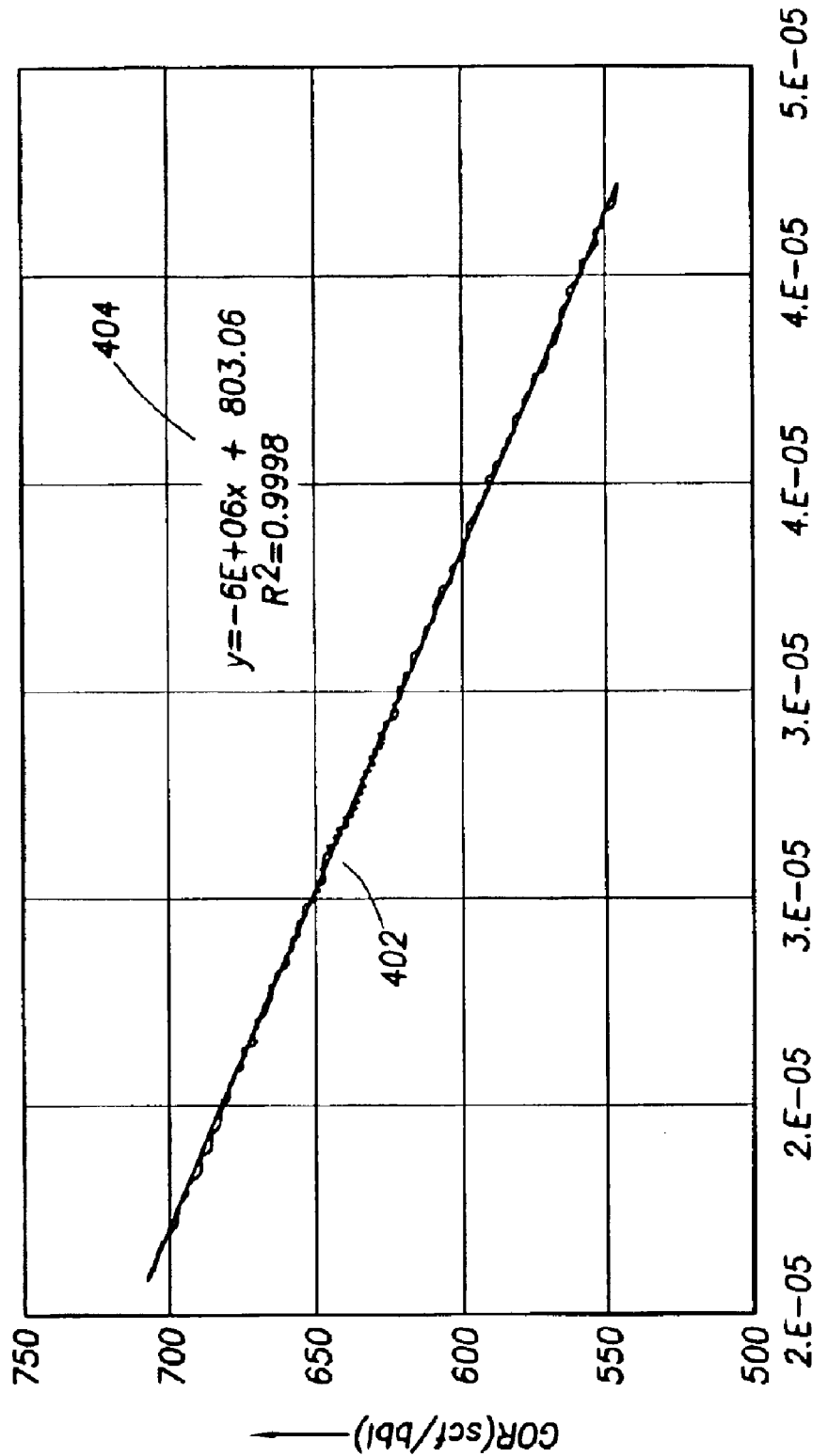
FIG. 4 shows a plot and analysis of the GOR versus the sampling parameter to the power of the exponential constant.

Once the exponential constant a is determined, the contamination free GOR, may be determined by plotting apparent GOR versus $t^{-a}$, as shown in FIG. 4, over the same fitting interval 306 used in FIG. 3. A linear curve fitting analysis 404 may be applied to the resulting plot 402 to determine the values of X and Y in Equation 1. As the elapsed time t goes to infinity, the term $Yt^{-a}$ approaches zero, and X is the contamination free GOR. In the particular example shown in FIG. 4, the contamination free GOR is calculated to be 803 scf/bbl.

Figure 10A:
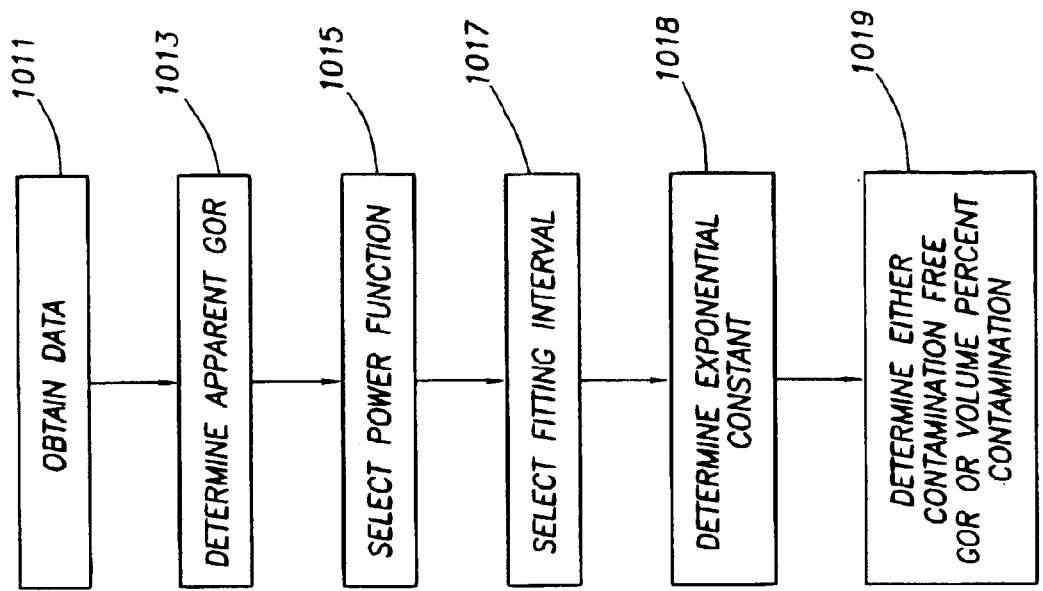
FIG. 10A shows one embodiment of a method according to the invention.

FIG. 10A shows one embodiment of a method according to the invention. The method includes obtaining data related to the optical density at a plurality of times for a fluid sample at a methane peak and at an oil peak (shown at step 1011). The data may be obtained by measuring the OD of a fluid sample as it is withdrawn. Next, the method includes calculating the apparent GOR of the fluid sample at the plurality of times from the data (shown at step 1013), or it may be obtained by having such data provided for analysis. The method also includes selecting a power function of a sampling parameter for a buildup of the apparent gas-oil-ratio (shown at step 1015). This need not be perfomed in the exact order shown. The sampling parameter may be elapsed time, pumping time, pumpout volume, or any other sampling parameter that represents the sampling process.

The method next includes calculating the exponential constant of the power function based on the data (shown at step 1018). In some embodiments, this is be done by first selecting a fitting interval (shown at step 1017), plotting the left side of Equation 4 versus ln(t), and determining the slope of the curve over the selected fitting interval.

Finally, the method includes determining either the contamination free GOR and/or the percent contamination of the fluid sample (shown at step 1019). In some embodiments, the power function may be used to calculate the contamination free GOR. In at least one embodiment, the contamination free GOR is used to determine the percent contamination of the fluid sample. In other embodiments, the percent contamination may be determined directly without specifically determining the contamination free GOR. The apparent GOR can be provided for analysis from other measuring device such as NMR (Nuclear Magnetic Resonance) tool.

The present invention is not limited to a power function for GOR as shown in Equation 1. For example, an exponential function for GOR may also be used $$GOR = A - Be^{-nt} \quad \text{Eqn. 5}$$

Where A is the contamination free GOR, B is a constant related to the buildup of apparent GOR, t is the pumping time, and n is a constant. Again, t could be elapsed time, pumpout volume, or another useful sampling parameter. Taking the time derivative of Equation 5:

$$\frac{d(GOR)}{dt} = nBe^{-nt} \quad \text{Eqn. 6}$$

The right side of Equation 6 may be rearranged to give:

$$\frac{d(GOR)}{dt} = n(A - Be^{-nt}) + nA \quad \text{Eqn. 7}$$

Equation 5 may be substituted into Equation 7 to give:

$$\frac{d(GOR)}{dt} = -nGOR + nA \quad \text{Eqn. 8}$$

Equation 6 shows that at an infinite elapsed time, when the apparent GOR is the contamination free GOR, the time derivative of GOR is zero. Equation 8 shows that the time derivative of apparent GOR has a linear relationship with apparent GOR. Thus, by plotting the time derivative of apparent GOR versus apparent GOR and extrapolating the linear portion to where the derivative is zero, the contamination free GOR is obtained.

Figure 5:
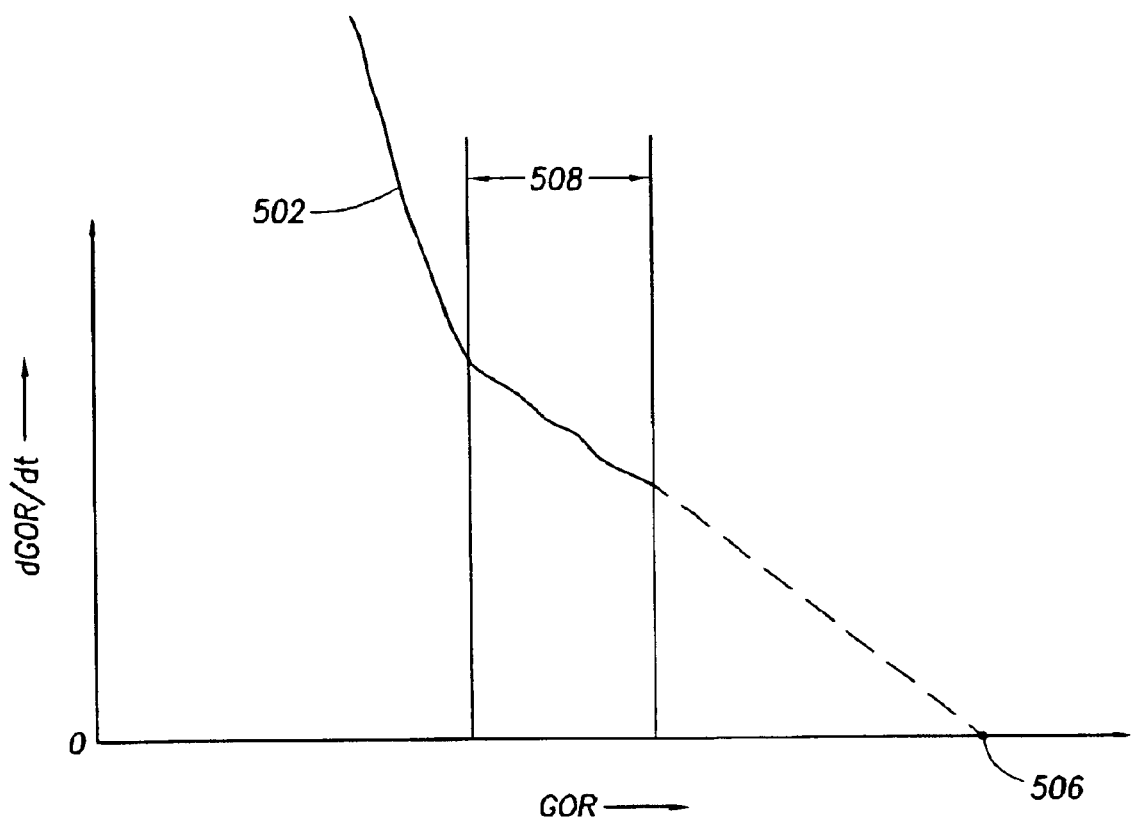
FIG. 5 shows a graph of the derivative of GOR with respect to a sampling parameter versus the GOR over a fitting interval.

FIG. 5 shows a graph of d(GOR)/dt versus GOR. The plot 502 is generated from apparent GOR data recorded while taking a fluid sample. A fitting interval, shown at 508, is selected over a portion of the plot 502 where the curve is substantially linear. As was described with reference to FIG. 3, those having ordinary skill in the art will appreciate the various methods for selecting a fitting interval. The portion of the plot 502 that is inside the fitting interval 508 is extrapolated to the point 506, where the derivative is zero. That point 506 is the contamination free GOR.

The volume percent contamination of dead oil of a fluid sample may be determined using the apparent GOR and the contamination free GOR. The contamination may be monitored during the sampling process to determine when the fluid sample has an acceptably low amount of contamination. When the contamination level is acceptably low, the fluid sample may be directed into a sample chamber for later analysis. The volume percent contamination may be determined using Equation 9:

$$\text{Vol \% Cont.} = \frac{GOR_0 - GOR}{GOR_0} \times 100 \quad \text{Eqn. 9}$$

Where $GOR_0$ is the contamination free GOR, and GOR is the apparent GOR. It is noted that the contamination may be determined once the contamination free GOR is determined using a power of time function, and exponential function, or any other function for determining the contamination free GOR.

FIG. 10B shows one embodiment of a method according to the invention. The method includes obtaining data related to the optical density at a plurality of times for a fluid sample at a methane peak and at an oil peak (shown at step 1021). The data may be obtained by measuring the OD of a fluid sample as it is withdrawn. Next, the method includes calculating the apparent GOR of the fluid sample a plurality of times from the data (shown at step 1023), or it may be obtained by having such data provided for analysis. The method also includes selecting an exponential function of a sampling parameter for a buildup of the apparent gas-oil-ratio (shown at step 1025). This need not be performed in the exact order shown. The sampling parameter may be elapsed time, pumping time, pumpout volume, or any other sampling parameter that represents the sampling process.

Finally, the method includes determining either the contamination free GOR and/or the percent contamination of the fluid sample (shown at step 1027). In some embodiments, the exponential function may be used to calculate the contamination free GOR. In at least one embodiment, the contamination free GOR is used to determine the percent contamination of the fluid sample. In other embodiments, the percent contamination may be determined directly without specifically determining the contamination free GOR.

Determining GOR from CGA

One or more embodiments of the present invention are related to determining GOR of an in-situ petroleum fluid using a Condensate and Gas Analyzer ("CGA"). A CGA tool uses specific wavelengths of electromagnetic radiation, preferably at specific resonance peaks for molecular vibration absorption of the constituents to be analyzed, to determine mass concentrations of the constituents of the fluid sample. Typically, a CGA is used to analyze the amount of methane ("$C_1$"), non-methane gaseous hydrocarbons (ie., ethane, butane, propane, and pentane) ("$C_{25}$"), liquid phase hydrocarbons (hexane and heavier hydrocarbon molecules) ("$C_{6+}$"), and carbon dioxide ("$CO_2$").

One or more embodiments of the present invention use the mass concentrations of the $C_1$, $C_{25}$, $C_{6+}$, and $CO_2$ components in a fluid sample to predict the volumes occupied by the gaseous phase and the liquid phase at the standard conditions. The volumes of the gaseous and liquid phases enable the determination of the GOR of the fluid sample.

The GOR is a function of the mass concentrations of methane ("$m_1$"), non-methane gaseous hydrocarbons ("$m_{25}$"), liquid phase hydrocarbons ($m_{6+}$), and carbon dioxide ("$m_{CO2}$"). A GOR estimation using component concentrations can be generally expressed as a function of the mass concentrations: GOR=$f(m_1, m_{25}, m_{6+}, m_{CO2})$. The actual formula may have an infinite number of forms, depending on the set of assumptions about the fluid and the particular equation of state used for the calculation.

In one or more embodiments of the invention, the GOR function is determined using the following assumptions:

1. The reservoir fluid may be approximated as a combination of four groups of molecules: $C_1$, $C_{25}$, $C_{6+}$, and $CO_2$.
2. The partial mass concentrations of the four groups of molecules are measurable with the CGA.
3. The $C_1$, $C_{25}$, and $CO_2$ molecule groups are entirely in the gaseous phase at the standard condition.
4. The $C_{6+}$ molecule group is entirely in the liquid phase at the standard condition.
5. The mass distribution within the $C_{25}$ molecule group is: $m_2 : m_3 : m_4 : m_5 \equiv 4:3:2:1$ (133:68:34:14 in molar ratio).
6. The density of the liquid phase is 0.75 g/cm$^3$.
7. The gaseous phase obeys the Real Gas Law: PV=znRT.

The Real Gas Law may be converted to the Ideal Gas Law by using 1 for the constant z. Alternatively, the constant z may be any value that is determined to provide a better estimate of the gaseous phase. In the following examples, z is taken to be one, although those having ordinary skill in the art will realize that other values of z may be used without departing from the scope of the invention.

Using assumption 7, the Real Gas Law is applied to the constituents of the gaseous phase to obtain Equations 1015, where n, the number of moles, is equal to the constituent mass divided by its molecular weight:

$$P_1 V_g = (m_2/16) RT$$

$$P_2 V_g = (m_2/30) RT$$

$$P_3 V_g = (m_3/44) RT$$

$$P_4 V_g = (m_4/58) RT$$

$$P_5 V_g = (m_5/72) RT$$

$$P_{CO2} V_g = (m_{co2}/44) RT \quad \text{Eqn. 10}$$

Where $P_1$, $P_2$, $P_3$, $P_4$, $P_5$, and $P_{CO2}$ are the partial pressures of the constituents of the gaseous phase, and $V_g$ is the volume of the gaseous phase at the standard condition. The partial pressures of the gaseous phase sum to one atmosphere of pressure (ie., the pressure at the standard condition):

$$P_1+P_2+P_3+P_4+P_5+P_{CO2}=1[\text{atm}] \quad \text{Eqn. 11}$$

Assumption 5 provides the mass ratios of the constituents of the gaseous phase:

$$m_2=0.4m_{25}; \; m_3=0.3m_{25}; \; m_4=0.2m_{25}; \; m_5=0.1m_{25} \quad \text{Eqn. 12}$$

The GOR, can be calculated as the ratio of the volume of gas ($V_g$) to the volume of liquid ($V_l$). The volume of gas ($V_g$) can be determined by solving Equations 10 and 11 for $V_g$ (seven unknowns and seven equations). The volume of the liquid phase ($V_l$) is equal to its mass ($m_{6+}$) divided by its density. The ratio of $V_g/V_l$ gives:

$$\text{GOR\_CGA} = k \left( \frac{0.625 m_1 + 0.250 m_{2-5} + 0.227 m_{CO_2}}{m_{6+}} \right) \quad \text{Eqn. 13}$$

Where k is a constant based on the assumptions above. For English units[scf/bbl], k=9,972; for metric units[m$^3$(gas)/m$^3$(liquid)], k=1,776. The CGA measurements provide $m_1$, $m_{25}$, $m_{6+}$, and $m_{CO2}$. These values may be used with Equation 13 to provide an estimate of the GOR.

The assumptions are used to formulate many of the equations above. It is noted that if one or more of these assumptions is modified, the resulting equations will also be different. For example, if the ratios in Assumption 5 are changed (e.g. m2:m3:m4:m5≡2.5:1.7:1.5:1.0), Equation 12 will reflect the new assumption:

$$m_2=0.37m_{25}; \; m_3=0.25m_{25}; \; m_4=0.23m_{25}; \; m_5=0.15m_{25} \quad \text{Eqn. 12a}$$

Using Equation 12a, Equation 13 would become:

$$\text{GOR\_CGA} = k \left( \frac{0.625 m_1 + 0.241 m_{2-5} + 0.227 m_{CO_2}}{m_{6+}} \right) \quad \text{Eqn. 13a}$$

Where the constant k would be 9,972 for units of scf/bbl. Those having ordinary skill in the art will understand that the assumptions may be changed and the resulting equations for GOR will be correspondingly different.

In one or more embodiments, the present invention enables the determination of GOR by accounting for a portion of hexane ($C_6$), heptane ($C_7$), octane ($C_8$), and nonane ($C_9$) to be vaporized at the standard condition. When portions of these constituents are in the gaseous phase, the volume of the liquid phase is reduced, and the GOR is increased.

A formula for expressing GOR as a function of the CGA measurements, where portions of $C_6$ through $C_9$ are in the gaseous phase, may be derived using certain assumptions, in addition to those above:

1. $C_1$, $C_{25}$, and $CO_2$ are entirely in the gaseous phase after the fluid is flashed at the standard condition.
2. After the fluid is flashed, the liquid phase contains 4 mol % $C_6$, 5 mol % $C_7$, 7 mol % $C_8$, and 8 mol % $C_9$.
3. In the gaseous phase, the vapors of $C_6$, $C_7$, $C_8$, and $C_9$ are in equilibrium with the liquid phase.
4. The density of the liquid phase is 0.8 g/cm$^3$.
5. The gaseous phase obeys the Real Gas Law (PV=znRT).

Using these assumptions, a formula for expressing GOR as a function of the CGA measurements may be derived:

$$\text{GOR\_CGA} = k \left( \frac{\frac{m_1}{16.0} + \frac{m_{2-5}}{40.1} + \frac{m_{CO_2}}{44.0}}{m_{6+} - 0.782 \left( \frac{m_1}{16.0} + \frac{m_{2-5}}{40.1} + \frac{m_{CO_2}}{44.0} \right)} \right) \quad \text{Eqn. 14}$$

Where k is a constant based on the particular assumptions used and on the desired units. For assumptions 15 above and unit of scf/bbl, k=107,285. For metric units of m$^3$(gas)/m$^3$(liquid), k=19,107. The CGA measurements provide $m_1$, $m_{25}$, $m_{6+}$, and $m_{CO2}$. In some embodiments, these measurements are used with Equation 14 to provide an estimation of the GOR of a fluid sample.

It will be understood that functions, other than the function shown in Equation 14, may be used without departing from the scope of the present invention. The exact form of the function depends on the particular assumptions made.

For example, mole fractions other than those in Assumption 2 may be used to derive an equation similar to or the same as Equation 14. Additionally, constituents heavier that $C_9$ may be present in the vaporized or gaseous phase. For example, $C_{11}$ and $C_{12}$ may be vaporized and may be accounted for in Assumption 2. Also, the estimation of the density may be varied from 0.8 g/cm$^3$. Those having ordinary skill in the art will be able to devise other assumptions and other functions, without departing from the scope of the present invention.

Methods for determining GOR using a CGA may be used in connection with methods for determining the contamination free GOR and methods for monitoring the contamination of a fluid sample using GOR. It is observed, however, that methods for determining the contamination free GOR and methods for monitoring the contamination of a fluid sample using GOR may be used with any method for determining GOR and are not limited to methods for determining GOR using a CGA. The apparent GOR can be provided for analysis from any resources such as NMR tool.

FIG. 10C shows one embodiment of a method according to the invention. The method first includes obtaining data related to a methane mass component, a non-methane gaseous hydrocarbon mass component, a liquid phase hydrocarbon mass component, and a carbon dioxide mass component of a fluid sample at a plurality of times (shown at step 1031).

In some embodiments, the method next includes making assumptions about the formation fluid constituents (shown at step 1033), and determining an equation for the GOR that is a function of the methane mass component, the non-methane gaseous hydrocarbon mass component, the liquid phase hydrocarbon mass component, and the carbon dioxide mass component (shown at step 1035). It is noted that making assumptions and determining an equation for GOR may be accomplished before or after the data is obtained.

Finally, the method includes calculating the GOR based from the ratio of the methane mass component, the non-methane gaseous hydrocarbon mass component, and the carbon dioxide mass component to the liquid phase hydrocarbon mass component (shown at step 1037).

Contamination Monitoring from CGA

In one or more embodiments of the invention, measurements from a CGA may be used for contamination monitoring for gas condensate sampling in an OBM well. The major component of downhole gas is methane, and very few types of downhole gas contain significant liquid components. OBM, on the other hand, usually contains no methane and is composed entirely of liquid phase hydrocarbons. Thus, the trend during sampling is for the $C_1$ to buildup and for the $C_{6+}$ to build down. The CGA measured the mass concentration of methane $m_1$ and the mass concentration of liquid phase hydrocarbons $m_6$.

Figure 6A:
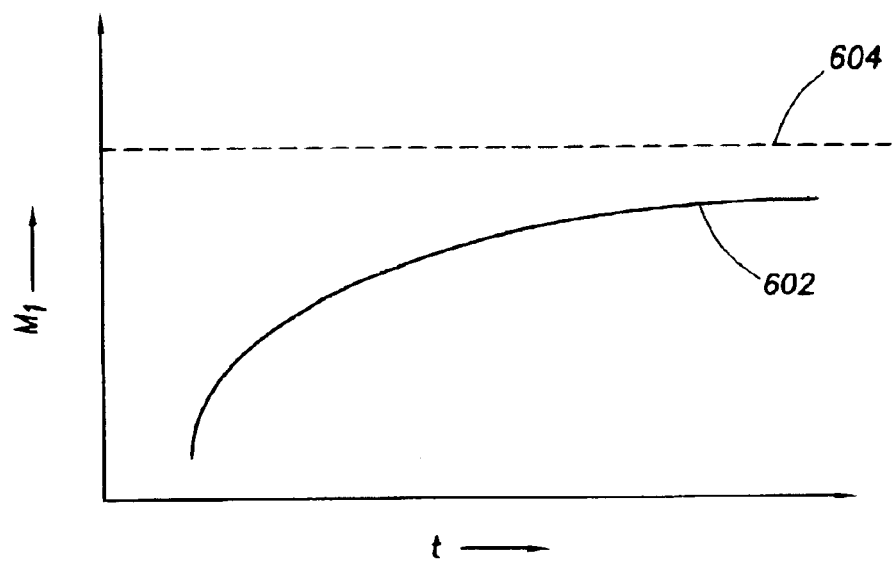
FIG. 6A shows a graph of the methane mass concentration versus a sampling parameter.
Figure 6B:
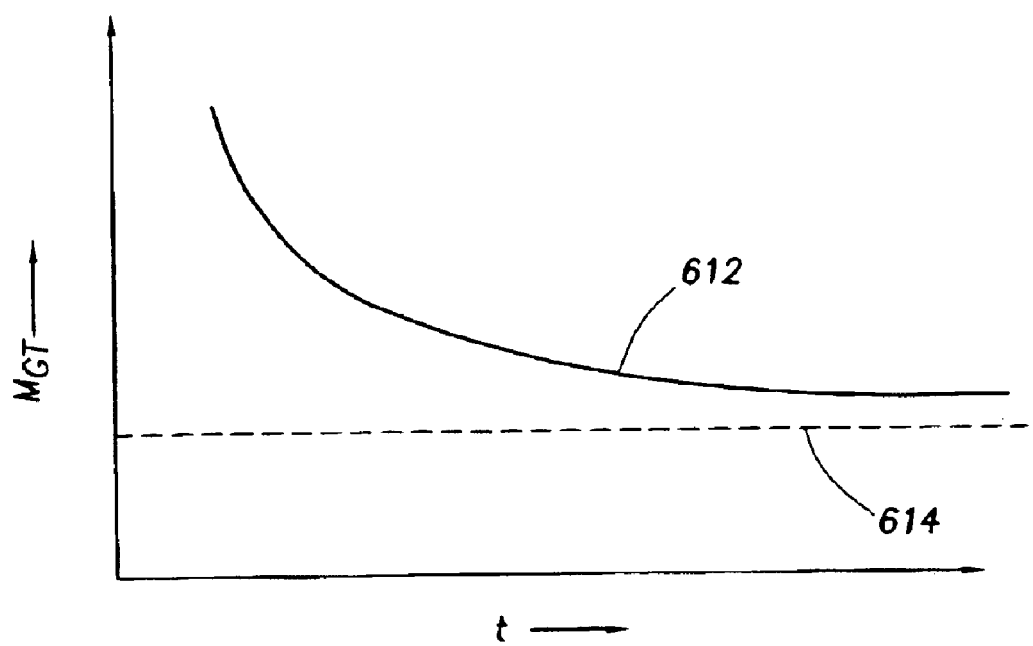
FIG. 6B shows a graph of the liquid phase hydrocarbon mass concentration versus a sampling parameter.

FIG. 6A shows that the $m_1$ (shown in $m_1$ plot 602) builds up with elapsed time during the sampling process. The $m_1$ asymptotically approaches the contamination free $m_1$ (shown as dashed line 604). Similarly, FIG. 6B shows that the $m_{6+}$ (shown in $m_{6+}$ plot 612) builds down with elapsed time during the sampling process. The $m_{6+}$ asymptotically approaches the contamination free $m_{6+}$ (shown as dashed line 614).

In some embodiments, the buildup of $m_1$ and the build-down of $m_{6+}$ may be modeled as power functions. For example, Equations 15 and 16, similar to Equation 1 for GOR, above:

$$m_1 = A - Bt^{-\alpha} \qquad \text{Eqn. 15}$$

$$m_{6+} = X + Yt^{-\beta} \qquad \text{Eqn. 16}$$

For Equation 15, $m_1$ is the measured concentration of methane, A is the contamination free $m_1$, $\beta$ is a constant related to the buildup of $m_1$, and $\alpha$ is an exponential constant. For Equation 16, $m_{6+}$ is the measured concentration of the liquid phase, X is the contamination free liquid phase, Y is a constant related to the build-down of $m_{6+}$, and $\beta$ is an exponential constant. It is noted, as above, t is a sampling parameter, and it may represent elapsed time, pumping time, pumpout volume, or any other sampling parameter that represents the pumpout process. Those having ordinary skill in the art will be able to devise other sampling parameters, without departing from the scope of the present invention.

In some embodiments, the exponential constants $\alpha$, $\beta$ are selected based on the estimated depth of mud filtrate invasion. In some embodiments, the constants $\alpha$, $\beta$ may be between 0.1 and 2.0. In at least one embodiment, one or both of the exponential constants $\alpha$, $\beta$ are about 0.5. For shallow invasion, it may be desirable to have lower exponential constants, e.g., $\alpha=\frac{1}{3}$ or $\beta=\frac{1}{3}$. For deep invasion, it may be desirable to have higher exponential constants, e.g. $\alpha=\frac{2}{3}$, $\beta=\frac{2}{3}$. Once the exponential constants are selected, the values of the constants in Equations 15 and 16 may be mathematically determined using sample data.

Figure 8A:
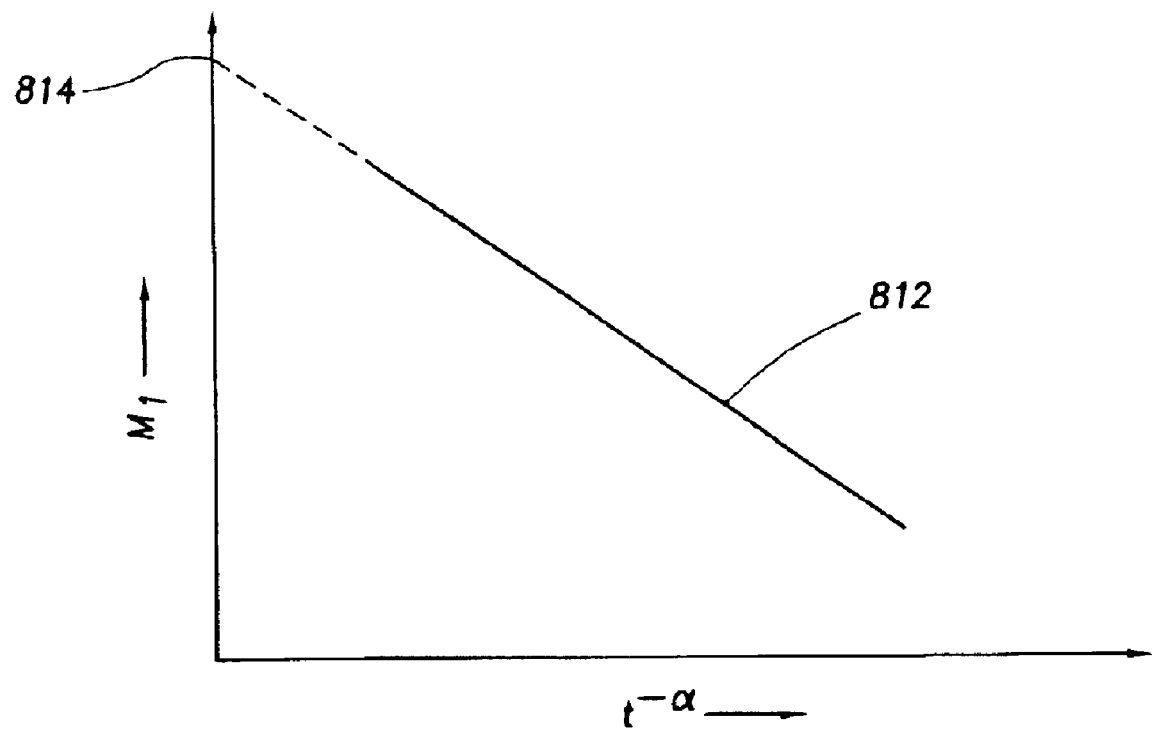
FIG. 8A shows a plot of the methane mass concentration versus the sampling parameter to the power of the exponential constant.
Figure 8B:
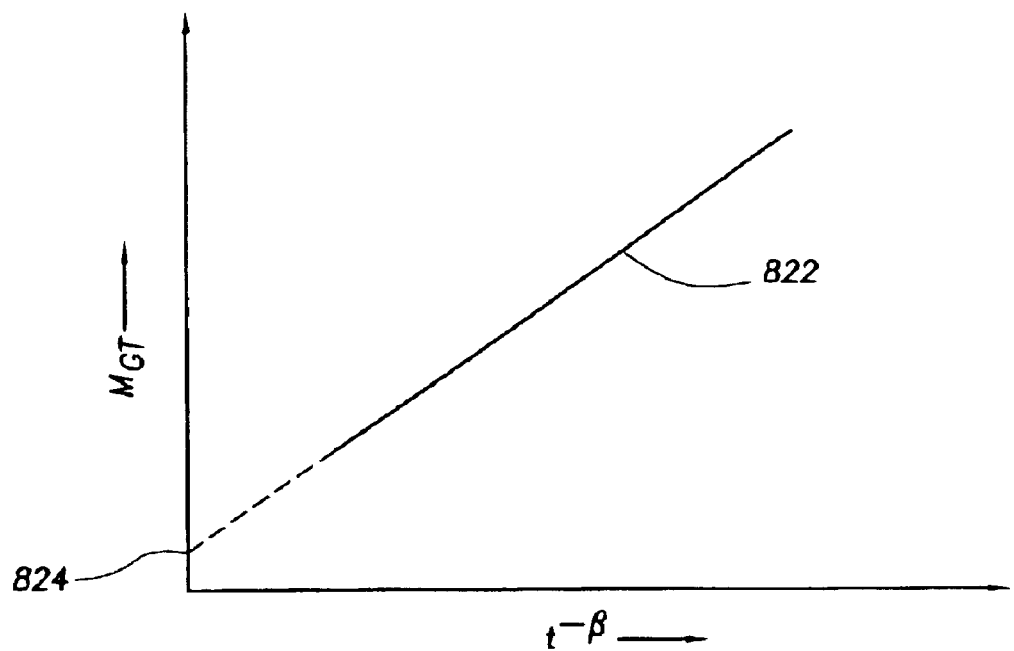
FIG. 8B shows a plot of the liquid phase hydrocarbon mass concentration versus the sampling parameter to the power of the exponential constant.

One method for determining the values of the contamination free $m_1$ and the contamination free $m_6+$ is shown in FIGS. 8A and 8B. FIG. 8A shows a graph of $m_1$ versus $t^{-\alpha}$. The relationship, as can be seen from Equation 15 and in FIG. 8A, is a linear relationship. An $m_1$ data plot 812 may be generated by a linear fit to $m_1$ and $t^{-\alpha}$ data points. The $m_1$ data plot 812 may be linearly extrapolated to $t^{-\alpha}=0$, where t is infinite. As t approaches infinity, $m_1$ approaches the contamination free $m_1$ (shown at the point 814). Similarly, as shown the graph in FIG. 8B, an $m_{6+}$ data plot 822 may be generated by a linear fit to $m_{6+}$ and $t^{-\beta}$ data points. The $m_{6+}$ data plot 822 may be linearly extrapolated to $t^{-\beta}=0$, where t is infinite. As t approaches infinity, $m_{6+}$ approaches the contamination free $m_{6+}$ (shown at the point 824).

In alternative embodiments, one or both of the exponential constants $\alpha$, $\beta$ may be measured. With the same manipulations used to transform Equation 1 into Equation 4, Equations 15 and 16 may be transformed into Equations 17 and 18:

$$\ln\left(\frac{d(m_1)}{d\ln(t)}\right) = \ln(\alpha) + \ln(B) - \alpha\ln(t) \qquad \text{Eqn. 17}$$

$$\ln\left(-\frac{d(m_{6+})}{d\ln(t)}\right) = \ln(\beta) + \ln(Y) - \beta\ln(t) \qquad \text{Eqn. 18}$$

Figure 7A:
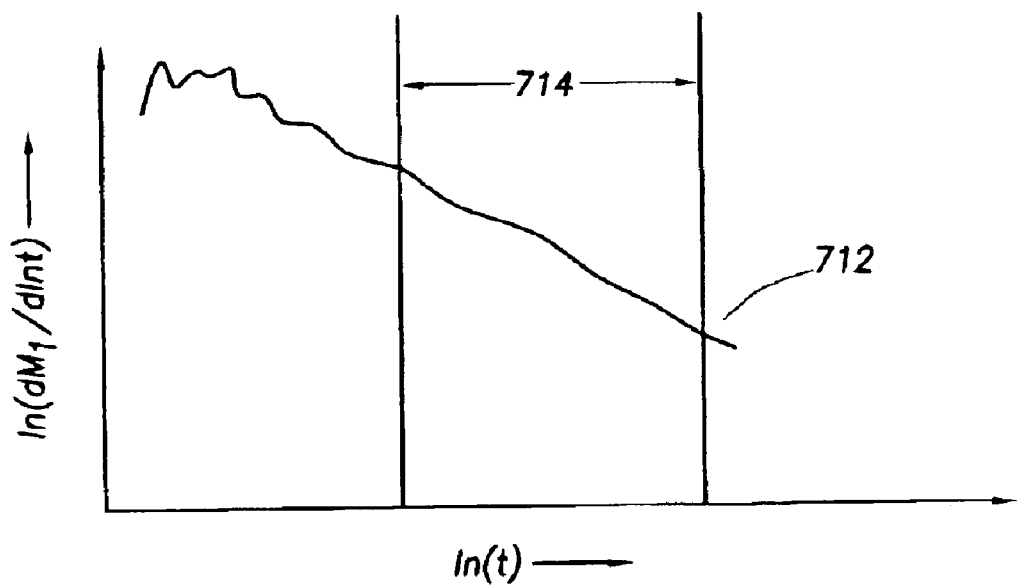
FIG. 7A shows a graph of the natural log of the methane mass concentration with respect to the natural log of a sampling parameter versus the natural log of the sampling parameter over a fitting interval.

Equation 17 shows that there is a linear relationship between $\ln(d(m_1)/d \ln (t))$ and $\ln(t)$. FIG. 7A shows a graph of $\ln(d(m_1)/d \ln(t))$ versus $\ln(t)$. The plot 712 of the data has a linear relationship over a portion of the plot, and the slope of the linear section provides the exponential constant $\alpha$. The slope of the plot 712 may be determined over a fitting interval, shown graphically at 714. Those having ordinary skill in the art will be able to devise methods of selecting a fitting interval. Once the exponential constant $\alpha$ is determined, the contamination free $m_1$ may be determined by plotting $m_1$ versus $t^{-\alpha}$ (812 in FIG. 8A) over the same fitting interval 714.

Figure 7B:
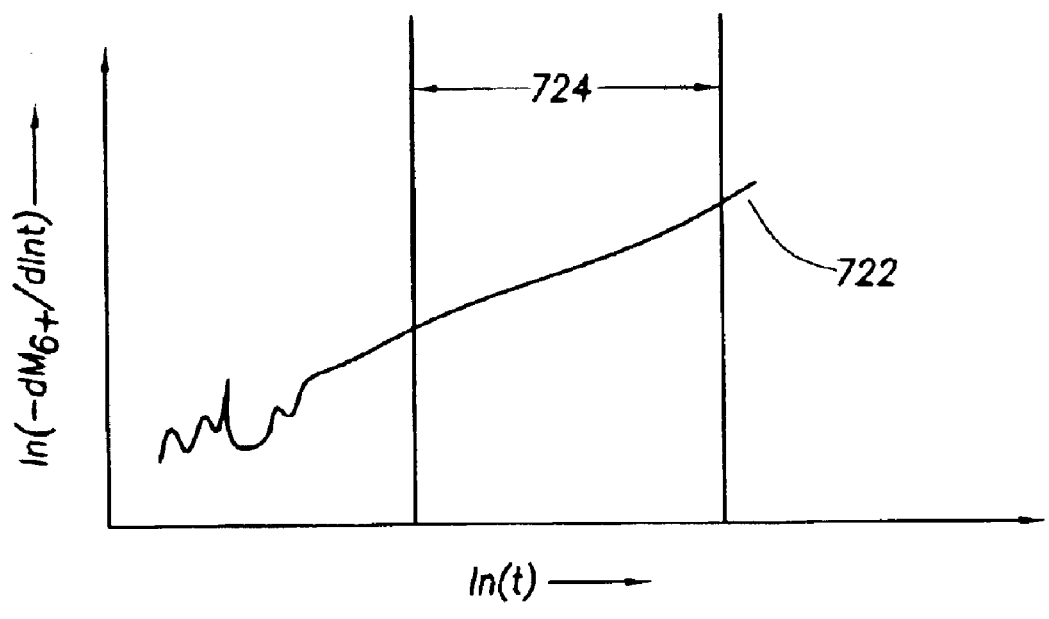
FIG. 7B shows a graph of the natural log of the liquid phase hydrocarbon mass concentration with respect to the natural log of a sampling parameter versus the natural log of the sampling parameter over a fitting interval.

Similarly, Equation 18 shows that there is a linear relationship between $\ln(-d(m_{6+}) /d \ln(t))$ and $\ln(t)$. FIG. 7B shows a graph of $\ln(-(d(m_{6+}))/d \ln(t))$ versus $\ln(t)$. The plot 722 of the data has a linear relationship over a portion of the plot, and the slope of the linear portion of the plot 722 provides the exponential constant $\beta$. The slope of the plot 722 may be determined over a fitting interval 724. Once the exponential constant β is determined, the contamination free $m_{6+}$ may be determined by plotting $m_{6+}$ versus $t^{-\beta}$ (822 in FIG. 8B) over the same fitting interval 724.

Figure 10D:
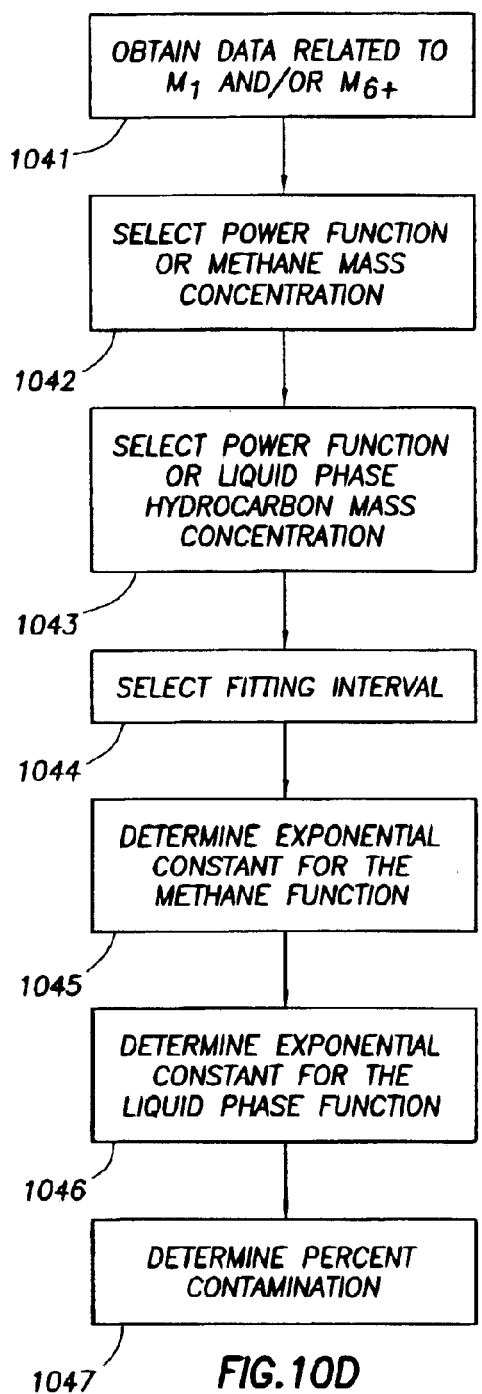
FIG. 10D shows another embodiment of a method according to the invention.

FIG. 10D shows one embodiment of a method according to the invention. The method includes obtaining data related to the mass concentration of methane and the mass concentration of liquid phase hydrocarbons for a fluid sample at a plurality of times (shown at step 1041). The data may be obtained by monitoring a fluid sample as it is withdrawn, or it may be obtained by having such data provided for analysis. Next, the method includes selecting a methane power function of a sampling parameter for the methane mass concentration (shown at step 1042) and selecting a liquid phase power function of the sampling parameter for the liquid phase hydrocarbon mass concentration (shown at step 1043). These need not be performed in the exact order shown. The sampling parameter may be elapsed time, pumping time, pumpout volume, or any other sampling parameter that represents the sampling process.

The method next includes determining the exponential constant of the methane power function (shown at step 1045) and determining the exponential constant of the liquid phase power function (shown at step 1046). In some embodiments, this is be done by first selecting a fitting interval (shown at step 1044), plotting the left side of Equations 17 and 18 versus ln(t), and determining the slopes of the curves over the selected fitting interval.

Finally, the method includes determining the percent contamination of the fluid sample (shown at step 1047).

In one or more embodiments, the concentrations of $m_1$ and $m_{6+}$ may be modeled as exponential functions, as shown in Equations 19 and 20:

$$m_1 = A - Be^{-\alpha t} \qquad \text{Eqn. 19}$$

$$m_{6+} = X + Ye^{\beta t} \qquad \text{Eqn. 20}$$

With the same manipulations used to transform Equation 5 into Equation 8, Equations 19 and 20 may be transformed into Equations 21 and 22.

$$\frac{d(m_1)}{dt} = -\alpha(m_1) + \alpha A \qquad \text{Eqn. 21}$$

$$\frac{d(m_{6+})}{dt} = -\beta(m_{6+}) + \beta X \qquad \text{Eqn. 22}$$

Figure 9A:
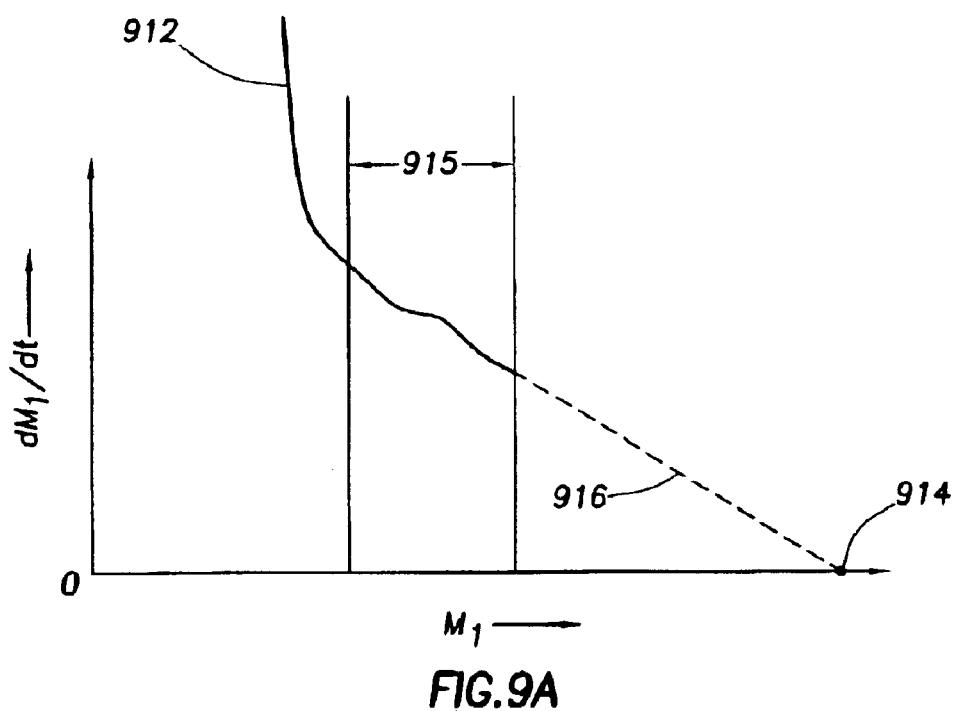
FIG. 9A shows a graph of the derivative of the methane mass concentration with respect to a sampling parameter versus the methane mass concentration.

Equation 21 shows that the derivative of $m_1$ with respect to t($dm_1/dt$) has a linear relationship with $m_1$. FIG. 9A shows a graph $dm_1/dt$ versus $m_1$. The plot 912 of the $m_1$ data is linear over a portion of the plot. A fitting interval 915 is selected over a portion of the plot 912 where the curve is substantially linear. The value of $m_1$ when the time derivative of $m_1$ is zero may be determined by linear extrapolation 916. This is the contamination free $m_1$, which is shown at 914.

Figure 9B:
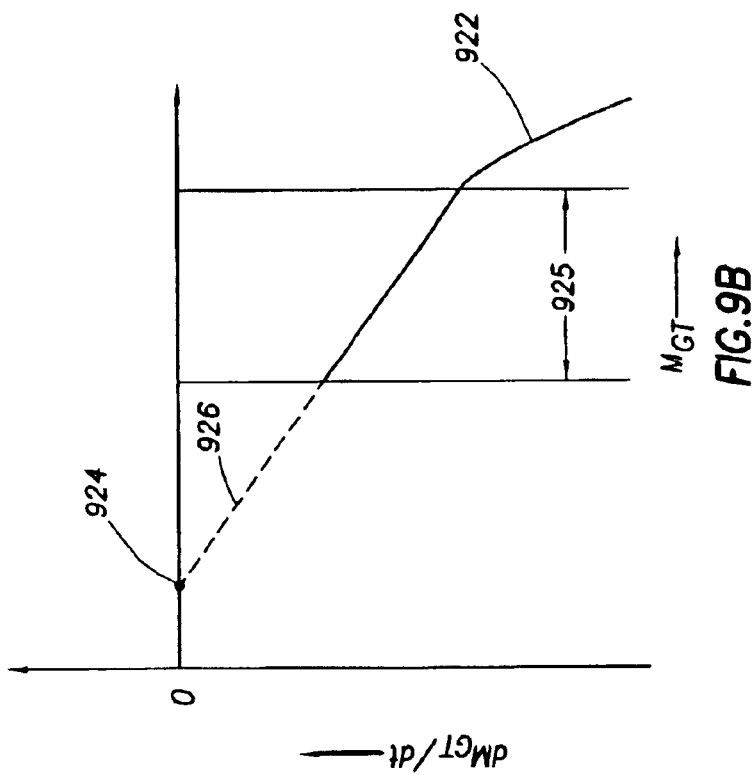
FIG. 9B shows a graph of the derivative of the liquid phase hydrocarbon mass concentration with respect to a sampling parameter versus the liquid phase hydrocarbon mass concentration.

Equation 22 shows that the derivative of $m_{6+}$ with respect to t(i.e., $dm_{6+}/dt$) has a linear relationship with $m_{6+}$. FIG. 9B shows a graph of $dm_{6+}/dt$ versus $m_{6+}$. A fitting interval 925 is selected over a portion of the plot 922 of the $m_{6+}$ data that is substantially linear. The value of $m_{6+}$ when the time derivative of $m_{6+}$ is zero may be determined by linear extrapolation 926 from the curve over the fitting interval 925. This is the contamination free $m_{6+}$, which is shown at 924.

The contamination of a fluid sample may be monitored using $m_1$ and $m_{6+}$ data. In some embodiments, the weight percent contamination is expressed as a function of the apparent $C_1$ or $C_{6+}$ and the contamination free values:

$$\% \text{ Cont.} = \frac{m_{1_0} - m_1}{m_{1_0}} \times 100 \qquad \text{Eqn. 23}$$

Where $m_{1_0}$ is the contamination free $m_1$, and $m_1$ is the apparent $m_1$.

$$\% \text{ Cont.} = \frac{m_6 - m_{6+_0}}{1 - m_{6+_0}} \times 100 \qquad \text{Eqn. 24}$$

Where $m_{6+0}$ is the contamination free $m_{6+}$, and $m_{6+}$ is the apparent $m_{6+}$.

In Equations 15 and 16, $m_1$ and $m_{6+}$ can be replaced by the color ratio, $R_{color}$, which is defined as:

$$R_{color} = \frac{OD_{color1} - OD_{base}}{OD_{color2} - OD_{base}} \qquad \text{Eqn. 25}$$

Where $OD_{color1}$ and $OD_{color2}$ are two different color channels, and $OD_{base}$ is the base channel for color. By replacing $m_1$ with color ratio, $R_{color}$, the contamination can be determined by:

$$\% \text{ Cont.} = \frac{R_{color\_0} - R_{color}}{R_{color\_0}} \times 100 \qquad \text{Eqn. 26}$$

Where $R_{color\_0}$ is the contamination free color ratio, which is derived in the same way as $m_1$.

Figure 10E:
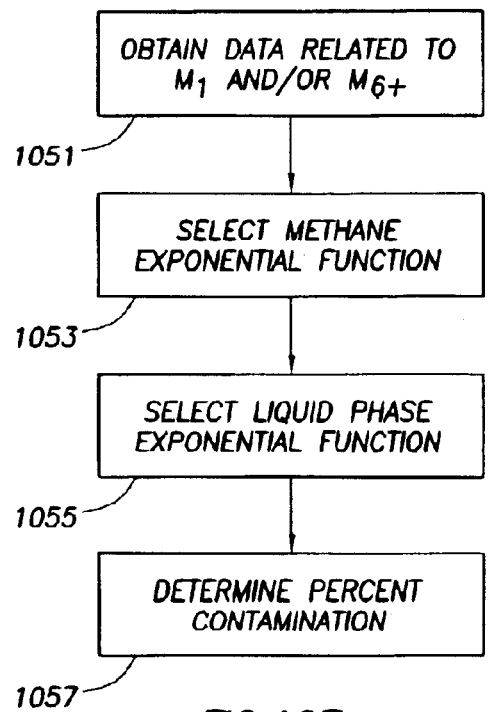
FIG. 10E shows another embodiment of a method according to the invention.

FIG. 10E shows a method according to one embodiment of the invention. The method includes obtaining data related to the mass concentration of methane and the mass concentration of liquid phase hydrocarbons for a fluid sample at a plurality of times (shown at step 1051). The data may be obtained by monitoring a fluid sample as it is withdrawn, or it may be obtained by having such data provided for analysis. Next, the method includes selecting a methane exponential function of a sampling parameter for the methane mass concentration (shown at step 1053) and selecting a liquid phase exponential function of the sampling parameter for the liquid phase hydrocarbon mass concentration (shown at step 1055). These need not be performed in the exact order shown. The sampling parameter may be elapsed time, pumping time, pumpout volume, or any other sampling parameter that represents the sampling process.

Finally, the method includes determining the percent contamination of the fluid sample (shown at step 1057).

Certain embodiments of the present invention may present one or more of the following advantages. Some embodiments enable the determination of the contamination free GOR. The contamination free GOR is a property of the formation fluid, and it may be determined without collecting a sample in a sample chamber. By doing so, the limited amount of sample collection volume in a formation testing tool may be conserved so that an increased amount of data may be collected in one run of the tool.

Advantageously, certain embodiments of the present invention enable contamination monitoring using apparent GOR. The GOR is more sensitive than color or methane analysis. The apparent GOR will continue to buildup in low contamination fluids, so that the a more accurate contamination level may be determined. Also, the apparent GOR is less sensitive to changes in the pumping rate of the fluid sample. Even when the pumping rate is slowed, the GOR may continue to buildup.

Advantageously, certain embodiments of the present invention enable the determination of a function of time that approximates the GOR. In these embodiments, the function may be used to determine how long it will take for a fluid sample to clean up to an acceptable level of contamination.

Advantageously, certain embodiments of the present invention enable the determination of apparent GOR using constituent mass concentrations. A function for apparent GOR may be based on assumptions about the components of the formation fluid. The GOR function enables a quick determination of GOR using commonly obtained formation fluid data.

Advantageously, certain embodiments of the present invention enable contamination monitoring using methane and liquid hydrocarbon mass concentrations. The contamination of a fluid sample may be monitored without the need to collect additional data for that purpose.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining properties of a formation fluid, comprising:
   obtaining data related to an optical density at a methane peak and an optical density at an oil peak for a fluid sample at a plurality of times;
   calculating an apparent gas-oil-ratio of the fluid sample from the optical density of the fluid sample at the methane peak and the optical density of the fluid sample at the oil peak at more than one of the plurality of times;
   selecting a power function of a sampling parameter for a buildup of the apparent gas-oil-ratio;
   calculating an exponential constant of the power function based on the data; and
   determining at least one selected from the group consisting of a contamination free gas-oil-ratio and a percent contamination.

2. The method of claim 1, wherein the sampling parameter is one selected from the group consisting of elapsed time, pumping time, and pumpout volume.

3. The method of claim 1, wherein determining the exponential constant comprises selecting a fitting interval for a plot of logarithm of a derivative of the gas-oil-ratio with respect to a natural log of the sampling parameter versus the natural log of the sampling parameter and determining the slope of the plot over the fitting interval.

4. The method of claim 3, wherein the fitting interval is automatically selected.

5. The method of claim 1, wherein the sampling parameter is one selected from the group consisting of a pumping time and an elapsed time, and further comprising determining a time when the fluid sample will comprise an acceptably low volume percent contamination.

6. The method of claim 1, wherein the sampling parameter is a pumpout volume and further comprising determining a pumpout volume where the fluid sample will comprise an acceptably low volume percent contamination.

7. The method of claim 1, wherein determining at least one selected from the group consisting of the contamination free gas-oil-ratio and the volume percent contamination comprises determining the contamination free gas-oil-ratio and further comprising extrapolating the gas-oil-ratio versus the sampling parameter to the power of the exponential constant to a point where the sampling parameter to the power of the exponential constant equals zero.

8. A method for determining properties of a formation fluid, comprising:
   obtaining data related to an optical density at a methane peak and at an optical density at an oil peak for a fluid sample at a plurality of times;
   calculating an apparent gas-oil-ratio of the sample fluid at the plurality of times based on the data;
   selecting an exponential function of a sampling parameter for a buildup of the apparent gas-oil-ratio; and
   linearly extrapolating the gas-oil-ratio to a point where a derivative of the exponential function with respect to the sampling parameter is zero.

9. The method of claim 8, wherein the sampling parameter is one selected from the group consisting of elapsed time, pumping time, and pumpout volume.

10. The method of claim 8, further comprising determining a percent contamination of the fluid sample.

11. The method of claim 8, wherein the sampling parameter is one selected from the group consisting of a pumping time and an elapsed time, and further comprising determining a time when the fluid sample will comprise an acceptably low volume percent contamination.

12. The method of claim 8, wherein the sampling parameter is a pumpout volume and further comprising determining a pumpout volume where the fluid sample will comprise an acceptably low volume percent contamination.

13. A method for determining a gas-oil-ratio of a fluid sample, comprising:
   obtaining data related to a methane mass component, a non-methane gaseous hydrocarbon mass component, a liquid phase hydrocarbon mass component, and a carbon dioxide mass component at a plurality of times; and
   determining the gas-oil-ratio from the ratio of the methane mass component, the non-methane gaseous hydrocarbon mass component, and the carbon dioxide mass component to the liquid phase hydrocarbon mass component.

14. The method of claim 13, wherein the determining the gas-oil-ratio comprises using a function of the methane mass concentration, the non-methane gaseous hydrocarbon mass component, the liquid phase hydrocarbon mass component, and the carbon dioxide mass component.

15. The method of claim 13, wherein the function is based on assumptions about formation fluid components.

16. The method of claim 15, wherein the assumptions comprise:
   that the fluid sample may be approximated as a combination of a methane molecule group, a non-methane gaseous hydrocarbon molecule group, a liquid phase hydrocarbon molecule group, and a carbon dioxide molecule group;
   that the methane molecule group, the non-methane gaseous hydrocarbon molecule group, and the carbon dioxide molecule group are in the gaseous phase at a standard condition;
   that the liquid phase hydrocarbon molecule group is entirely in the liquid phase at the standard condition;
   that a mass distribution between the ethane molecule, propane molecule, butane molecule and pentane molecule is about 4 to 3 to 2 to 1, respectively;

that a density of the liquid phase hydrocarbon molecule group is about 0.75 g/cm³; and that the methane molecule group, the non-methane gaseous hydrocarbon molecule group, and the carbon dioxide molecule group obey an Ideal Gas Law.

17. The method of claim 15, wherein the assumptions comprise:

that a methane molecule group, a non-methane gaseous hydrocarbon molecule group, and a carbon dioxide molecule group are entirely in the gaseous phase after the fluid is flashed at the standard condition;

that after the fluid is flashed, the liquid phase contains 4 mol% hexane, 5 mol% septan; 7 mol % octane, and 8 mol % nonane;

that in the gaseous phase, the vapors of hezane, septane, octane, and nonane are in equilibrium with the liquid phase; and that the density of the liquid phase is 0.8 g/cm³.

18. A method for determining properties of a formation fluid, comprising:

obtaining data related to a mass concentration of methane and a mass concentration of liquid phase hydrocarbons for a fluid sample at a plurality of times;

calculating an apparent methane mass concentration and an apparent liquid phase hydrocarbon mass concentration of the fluid sample at each of the plurality of times;

selecting a methane power function of a sampling parameter for a buildup of the apparent methane mass concentration;

selecting a liquid phase power function of the sampling parameter for a buildup of the apparent liquid phase hydrocarbon mass concentration;

determining an exponential constant of the methane power function based on the data;

determining an exponential constant of the liquid phase power function based on the data; and determining a percent contamination.

19. The method of claim 18, wherein the determining the exponential constant of the methane-power function based on the data comprises selecting the exponential constant of the methane power function to be between about 0.1 and 20, and wherein the determining the exponential constant of the liquid phase power function based on the data comprises selecting the exponential constant of the liquid phase power function to be between about 0.1 and 2.0.

20. The method of claim 18, wherein the determining the exponential constant of the methane power function based on the data comprises selecting the exponential constant of the methane power function to be about 0.5, and wherein determining the exponential constant of the liquid phase power function based on the data comprises selecting the exponential constant of the liquid phase power function to be about 0.5.

21. The method of claim 18, wherein the determining the exponential constant of the methane power function based on the data comprises selecting the exponential constant of the methane power function to be about ⅓ for a formation with a shallow invasion and ⅔ for a formation with a deep invasion, and wherein the detemiining the exponential constant of the liquid phase power function based on the data comprises selecting the exponential constant of the liquid phase power function to be about ⅓ for a formation with a shallow invasion and ⅔ for a formation with a deep invasion.

22. The method of claim 18, wherein the sampling parameter is one selected from the group consisting of elapsed time, pumping time, and pumpout volume.

23. The method of claim 18, wherein the determining the exponential constant of the methane power function comprises selecting a fitting interval for a methane plot of a natural log of a derivative of the methane mass concentration with respect to a natural log of the sampling parameter versus the natural log of the sampling parameter and determining a slop of the methane plot over the fitting interval, and wherein the determining the exponential constant of the liquid phase power function comprises selecting a fitting interval for a liquid phase plot of a natural log of a derivative of the liquid phase hydrocarbon mass concentration with respect to the natural log of the sampling parameter versus the natural log of the sampling parameter and determining a slope of the liquid phase plot over the fitting interval.

24. The method of claim 23, wherein the fitting interval for the methane plot is automatically selected and the fitting interval for the liquid phase plot is automatically selected.

25. The method of claim 18, wherein the sampling parameter is one selected from the group consisting of a pumping time and an elapsed time, and further comprising determining a time when the fluid sample will contain less than a predetermined level of contamination.

26. The method of claim 18, wherein the sampling parameter is a pumpout volume and further comprising determining a pumpout volume where the fluid sample will comprise an acceptably low volume percent contamination.

27. A method for determining properties of a formation fluid, comprising:

obtaining data related to a mass concentration of methane and a mass concentration of liquid phase hydrocarbons for a fluid sample at a plurality of times;

calculating an apparent methane mass concentration and an apparent liquid phase hydrocarbon mass concentration of the fluid sample at each of the plurality of times;

selecting a methane exponential function of a sampling parameter for a buildup of the apparent methane mass concentration;

selecting a liquid phase exponential function of the sampling parameter for a buildup of the apparent liquid phase hydrocarbon mass concentration; and determining a percent contamination from the data.

28. The method of claim 27, wherein the sampling parameter is one selected from the group consisting of elapsed time, pumping time and pumpout volume.

29. The method of claim 27, wherein the sampling parameter is one selected from the group consisting of a pumping time and an elapsed time, and further comprising determining a time when the fluid sample will contain less than a predetermined level of contamination.

30. The method of claim 27, wherein the sampling parameter is a pumpout volume and further comprising determining a pumpout volume where the fluid sample will contain less than a predetermined level of contamination.

* * * * *

UNITED STATES PATENT AND TRADEMARK OFFICE
CERTIFICATE OF CORRECTION

PATENT NO.    : 6,956,204 B2
DATED         : October 18, 2005
INVENTOR(S)   : Dong et al.

It is certified that error appears in the above-identified patent and that said Letters Patent is hereby corrected as shown below:

<u>Title page,</u>
Item [75], Inventors, "Peter S. Hageman" should read -- Peter S. Hegeman --.

Signed and Sealed this

Seventh Day of March, 2006

JON W. DUDAS
*Director of the United States Patent and Trademark Office*